United States Patent
Zhao et al.

(10) Patent No.: US 9,586,904 B2
(45) Date of Patent: Mar. 7, 2017

(54) PREPARATION OF (−)-HUPERZINE A

(71) Applicant: ZHEJIANG WANBANG PHARMACEUTICAL PLC., Wenling, Zhejiang (CN)

(72) Inventors: Shouming Zhao, Zhejiang (CN); Ping Chen, Zhejiang (CN); Shaoping Peng, Zhejiang (CN); Yinqiang Zhuang, Zhejiang (CN); Rongzhen Shi, Zhejiang (CN); Jinsheng Xie, Zhejiang (CN); Weihua Xie, Zhejiang (CN)

(73) Assignee: ZHEJIANG WANBANG PHARMACEUTICAL PLC. (CN)

( * ) Notice: Subject to any disclaimer, the term of this patent is extended or adjusted under 35 U.S.C. 154(b) by 0 days.

(21) Appl. No.: 14/905,331

(22) PCT Filed: Jun. 17, 2014

(86) PCT No.: PCT/CN2014/080092
§ 371 (c)(1),
(2) Date: Jan. 15, 2016

(87) PCT Pub. No.: WO2015/007129
PCT Pub. Date: Jan. 22, 2015

(65) Prior Publication Data
US 2016/0159745 A1  Jun. 9, 2016

(30) Foreign Application Priority Data
Jul. 15, 2013 (CN) .......................... 2013 1 0295691

(51) Int. Cl.
*C07D 221/22* (2006.01)
(52) U.S. Cl.
CPC ................. *C07D 221/22* (2013.01)
(58) Field of Classification Search
None
See application file for complete search history.

(56) References Cited

FOREIGN PATENT DOCUMENTS

| CN | 101130520 | 2/2008 |
|----|-----------|--------|
| CN | 101333190 | 12/2008 |
| CN | 102627605 | 8/2012 |
| CN | 103224467 | 7/2013 |
| CN | 103570621 | 2/2014 |

OTHER PUBLICATIONS

He, X.-C. et al Chin J Chem 2007 vol. 25 pp. 583-586.*
Written Opinion, Sep. 29, 2014, for Zhejiang Wanbang Pharmaceutical PLC, International Application No. PCT/CN2014/080092, filed Jun. 17, 2014.
International Search Report, Sep. 29, 2014, for Zhejiang Wanbang Pharmaceutical PLC, International Application No. PCT/CN2014/080092, filed Jun. 17, 2014.
Jul. 3, 2014 First Office Action, CN 201310295691.8.
Nov. 4, 2014 Second Office Action, CN 201310295691.8
He, X-C et al., 2007, Practical Tactics in Resolution of Racemates via Diastereorneric Salt Formation, Chinese Journal of Chemistry, 25, 583-586.
Zeng, F et al., 2000, Pogress in Synthesis and Structural Modification of Huperzine A, Progress in Chemistry, 12, 1, 63-76.

* cited by examiner

*Primary Examiner* — Heidi Reese
(74) *Attorney, Agent, or Firm* — Law Offices of Albert Wai-Kit Chan, PLLC

(57) ABSTRACT

The present invention relates to a method for preparing (−)-huperzine A. The method involves: allowing a mixture of (±)-huperzine A obtained from chemical synthesis and a chiral acid to form (±)-huperzine A chiral acid salt under suitable conditions; recrystallizing the chiral acid salt from an organic solvent and basifying with an alkali to obtain optically pure (−)-huperzine A. The method is convenient to operate and suitable for industrial production. The chemical purity and optical purity of (−)-huperzine A obtained by the method are each greater than 99.5%, satisfying the requirement for raw pharmaceutical purity in the pharmaceutical industry.

10 Claims, 9 Drawing Sheets

PREPARATION OF (−)-HUPERZINE A

This application is the National Phase of International Application No. PCT/CN2014/080092, filed Jun. 17, 2014, which claims the priority of Chinese Application No. 201310295691.8, filed Jul. 15, 2013. The entire contents and disclosures of the preceding applications are hereby incorporated by reference into this application. Throughout this application, various publications are referenced. Disclosures of these publications in their entireties are hereby incorporated by reference into this application in order to more fully describe the state of the art to which this invention pertains.

FIELD OF THE INVENTION

The present invention relates to the field of medicinal chemistry, particularly a method of resolving huperzine A. The method includes formation of a chiral acid salt with racemic huperzine A, followed by recrystallization and then basification to obtain (−)-huperzine A.

BACKGROUND OF THE INVENTION

Huperzine A is a highly active alkaloid isolated from *Melaleuca* tower of Lycopodiaceae plant [*Huperzia serrata* (Thunb) Thev.]. Optical isomer (−)-huperzine A is usually employed as a pharmaceutically active ingredient. The structural formula of (−)-huperzine A is as follows:

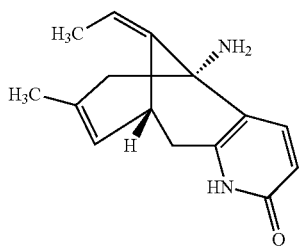 [SMILES: C/C=C1\C23CC(C)=C[C@H]2Cc2[nH]c(=O)ccc2[C@]13N]

The chemical name of (−)-huperzine A is: (5R,9R,11E)-5-amino-11-ethylidene-5,6,9,10-tetrahydro-7-methyl-5,9-methanocycloocta[β]pyridin-2-(IH)-one.

(−)-Huperzine A is a highly efficient and highly selective reversible inhibitor of acetylcholinesterase, can improve learning and memory efficiency, and can be used to treat a variety of neurological and psychiatric diseases.

(−)-Huperzine A tablets were launched in the Chinese market in 1995, and has been used for the treatment of Alzheimer's disease (AD) and memory disorders clinically. In other countries, huperzine A has been used as a food additive, and widely used as an active ingredient in functional drinks, with the purpose of improving the memory of the elderly and enhancing the reaction time of athletes. (−)-Huperzine A formulations can be used to improve learning and memory efficiency, and restore the functions of damaged neurons. It is mainly used for the treatment of myasthenia gravis, schizophrenia, dementia, benign memory impairment, etc.; in particular, amnesia and senile dementia, and effectively improving children's memories.

The amount of natural (−)-huperzine A in *Melaleuca* tower of Lycopodiaceae plant is merely about one in ten thousand, and the growing period of *Melaleuca* tower flora is up to 8-10 years. Simple extraction cannot meet the demand of the market; therefore, chemical synthesis is required in order to increase market supply.

The two strategies for chemical synthesis of (−)-huperzine A are asymmetric synthesis and racemic resolution method. Current asymmetric synthesis of (−)-huperzine A requires the use of expensive metal palladium catalyst and chiral ligands coordinated to palladium. The difficulties of recovering palladium catalyst, coupled with the high cost of preparation, isolation and purification of chiral ligands, form an obstacle to large-scale production of (−)-huperzine A. At present, such asymmetric synthesis can only be done in small laboratory scale, not suitable for large scale production, let alone providing the pharmaceutical industry with an industrial low-cost and convenient production of (−)-huperzine A.

Aside from asymmetric synthesis, the Patent CN101130520 reported a resolution approach to prepare (−)-huperzine A. Chang et al. first obtained racemic O-methyl-huperzine A by chemical synthesis, then formed diastereomeric salts between the racemic compound and an acidic resolving agent, (−)-2,3-dibenzoyl tartaric acid. Repeated recrystallization from organic solvent, followed by basifciation and deprotection, provided (−)-huperzine A. The reaction process is as follows:

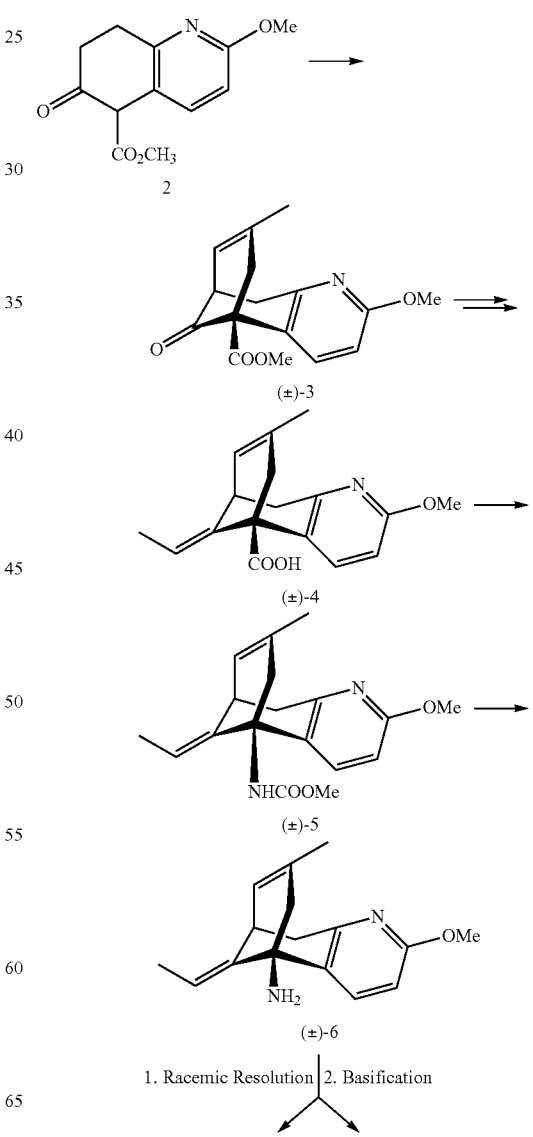

-continued

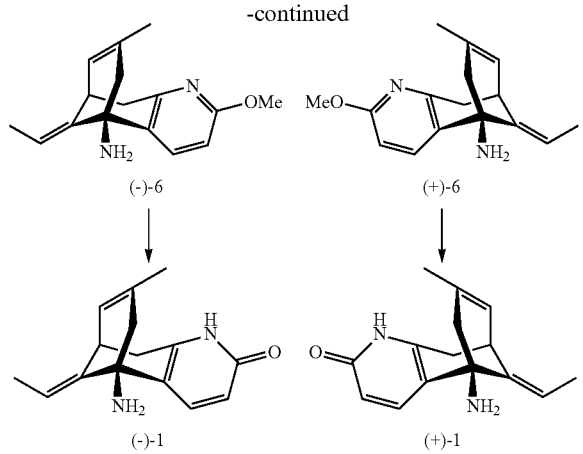

(-)-6  (+)-6

(-)-1  (+)-1

In the patent of Chang et al., the yield of intermediate (−)-O-methyl huperzine A after resolution is 16%. Obviously, during the preparation of (−)-huperzine A, creative systematic research was not conducted on the resolution approach, resulting in about 34% of the final product being not obtained in the first attempt. Although the total yield can be improved after recovery, basification and repeated resolution, the process involved complex operation, and the quality of the recovered material is difficult to control. Therefore, the process does not meet the production requirement of GMP, and is also difficult to satisfy the API production requirement of the pharmaceutical industry.

Because the preparation route for (±)-O-methyl huperzine A is more than 10 steps, the overall yield of (±)-O-methyl huperzine A through these steps is very low (<5%). In addition, a number of expensive raw materials have to be used, such as the raw material acrylonitrile (>4000 Yuan per kilogram), methylation reagent $Ag_2CO_3$ (>6000 Yuan per kilogram), 30% Pd/C (>1000 Yuan per kilogram), lithium aluminum hydride, (>1900 Yuan per kilogram), etc. The production cost of (±)-O-methyl huperzine A is extremely high. If the yield of (±)-O-methyl huperzine A is calculated according to the reference [Chinese J. Med. Chem., 1992, 2(2), 1] in CN101130520, the production cost is more than 140,000 Yuan per kilogram. The detailed calculation is as follows:

| Raw material | Amount/kg | Price (Yuan/kg) | Total cost/Yuan |
| --- | --- | --- | --- |
| Acrylonitrile | 45 | 900 | 40,500 |
| Ethyl acetoacetate | 90 | 63.4 | 5,706 |
| 30% Pd/C | 4.5 | 27,000 | 12,150 (recycling rate 90%) |
| Silver carbonate | 40 | 5,500 | 22,000 (recycling rate 90%) |
| Iodomethane | 50 | 700 | 35,000 |
| Lithium aluminum hydride | 6.5 | 1,950 | 12,675 |
| Sodium cyanide | 15 | 600 | 9,000 |
| 2-methacrylaldehyde | 4 | 500 | 2,000 |
| Diphenylphosphoryl azide | 12.0 | 450 | 5,400 |
| Total | | | ~140000 Yuan |

Based on the calculated cost as above, if (±)-O-methyl huperzine A is subject to chiral resolution based on the yield of 16%, the cost of the raw materials for (−)-O-methyl huperzine A will be increased from 280,000 Yuan/kg (a chiral resolution rate of 50% is used for calculation) to 870,000 Yuan/kg.

Since the chiral resolution yield has a decisive influence on the production cost for the final product (−)-huperzine A, it is very important to select proper procedures of chiral resolution. It is found by repeated experiments that the yield is relatively low via chiral resolution of (±)-O-methyl huperzine A and is difficult for further improvement. It is also found that (±)-huperzine A is rather poorly soluble in most solvents. This may be the reason why there has not been any report about chiral resolution in the last step.

The above experimental result indicates that direct chiral resolution of (±)-huperzine A is a highly challenging and creative task. After the inventors performed a number of screening investigations on resolving solvents, types of resolving agents, and resolving procedures, a method with an amazing >70% recycling rate of (−)-huperzine A was found by resolving a mixture of diastereomers: direct formation of a salt between (±)-huperzine A and a chiral acid in a proper solvent gives the (±)-huperzine A-chiral acid salt. (−)-Huperzine A with high purity is obtained after recrystallization and basification, and the yield of the target isomer is higher than 70%. Due to the increased yield, the production cost for (−)-huperzine A can be reduced to one half of that of current technology. In addition, the optical purity of the target product obtained by this method can be higher than 99.8%. The chemical purity can be higher than 99.5%. With further recrystallization, the purity can be higher than 99.9% and the amount of each impurity is lower than 0.02%. It fully meets the requirements for pharmaceutical raw materials.

SUMMARY OF THE INVENTION

This invention discloses a method of synthesizing (−)-huperzine A. The method includes the following steps: 1) formation of a salt between (±)-huperzine A and a chiral acid gives a (−)-huperzine A-chiral acid salt; and 2) basifying the (−)-huperzine A-chiral acid salt generates (−)-huperzine A.

(±)-Huperzine A in step 1) is part of the current technology, and can be prepared by the procedure described in CN101333190 with a production cost of 150 Yuan/gram. (±)-Huperzine A can also be purchased.

The chiral acid is any chiral acid which can form a stable salt with (±)-huperzine A for further preparation of (−)-huperzine A. The chiral acid can be selected from chiral organic acids and chiral inorganic acids, preferably the chiral acid is selected from D-dibenzoyl tartaric acid, D-tartaric acid, D-malic acid, D-mandelic acid and D-camphorsulfonic acid. The salt is obtained through the reaction between (±)-huperzine A and a chiral acid in a solvent, wherein the molar ratio of (±)-huperzine A to chiral acid is in the range of 1:0.5 to 1:2. The solvent is selected from ethanol, ethyl acetate, acetone, tetrahydrofuran, water and a mixture thereof. The preferred solvent is a mixed solvent system such as acetone-water or ethanol-water, wherein the acetone-water ratio is 1:1-5:1 and the ethanol-water ratio is 1:1-5:1.

The reaction conditions are as follows.

(±)-Huperzine A is suspended in a solvent with a ratio of compound to solvent of 1:5-1:15. After the suspension is homogeneously mixed by stirring, a chiral acid is added. After stirring for 0.5-2 h, the suspension is filtered. The solid is recrystallized to give (−)-huperzine A-chiral acid salt.

The solvent for recrystallization is selected from acetone, ethanol, ethyl acetate, water and a mixture thereof.

The method for basification in step 2) is as follows.

The (−)-huperzine A-chiral acid salt is added into water with a ratio of salt to water of 1:2 to 1:8. After the suspension is homogeneously mixed by stirring, a solution of sodium hydroxide is used to adjust the pH value to 9.0-10.0. After crystals are precipitated, the suspension is filtered to give a solid, which is then dried to give (−)-huperzine A.

A preferred method is as follows.

A method for synthesizing (−)-huperzine A includes the following steps:
1) Formation of a salt between (±)-huperzine A and a chiral acid to give a (−)-huperzine A-chiral acid salt; and 2) Basification of the (−)-O-huperzine A-chiral acid salt generates (−)-huperzine A.

The chiral acid in step 1) is selected from D-dibenzoyl tartaric acid, D-tartaric acid, D-malic acid, D-mandelic acid and D-camphorsulfonic acid. The formation of salt is achieved through the reaction between (±)-huperzine A and a chiral acid in a solvent. The solvent is selected from acetone-water or ethanol-water.

Preferably, the chiral acid in step 1) is D-dibenzoyl tartaric acid. The solvent in step 1) is selected from acetone-water and ethanol-water, wherein the acetone-water ratio is 1:1-5:1, the ethanol-water ratio is 1:1-5:1, and the (±)-huperzine A/chiral acid ratio is 1:0.5-1:2. More preferably, the acetone-water ratio is 1:1-3:1, the ethanol-water ratio is 1:1-3:1, and the (±)-huperzine A/chiral acid ratio is 1:0.75-1:1.5.

Most preferably, the acetone-water ratio is 1:1, the ethanol-water ratio is 1:1, and the (±)-huperzine A/chiral acid ratio is 1:0.8-0.9.

A more preferable method is as below.

(±)-Huperzine A is suspended in acetone-water or ethanol-water, wherein the acetone-water ratio is 1:1-5:1, the ethanol-water ratio is 1:1-5:1, and the (±)-huperzine A/solvent ratio by weight is 1:5-1:15. D-dibenzoyl tartaric acid is then added to form a salt, wherein the molar ratio of (±)-huperzine A/D-dibenzoyl tartaric acid is 1:0.5-1:2. After formation of a salt, the salt is filtered, washed and dried to give the (−)-huperzine A-chiral acid salt. The salt is added into water with a weight ratio of 1:2-1:8. After the suspension is homogeneously mixed by stirring, a solution of sodium hydroxide is used to adjust the pH value to 9.0-9.3. After crystals are precipitated, the suspension is filtered to give a solid, which is then dried to give (−)-huperzine A.

The most preferable method is as below.

(±)-Huperzine A is suspended in ethanol-water, wherein the ethanol-water ratio is 1:1. D-dibenzoyl tartaric acid is then added to form a salt, wherein the molar ratio of (±)-huperzine A/D-dibenzoyl tartaric acid is 1:1. After stirring for 1 h, the solid is filtered and recrystallized from anhydrous ethanol to give (−)-huperzine A-chiral acid salt. The salt is added into water with a weight ratio of 1:4. The pH value is adjusted to 9.0-9.3 by a 40% sodium hydroxide solution. The suspension is filtered and (−)-huperzine A is obtained after drying under vacuum.

The invention discovered that a chiral acid can be used as a resolving agent to obtain (−)-huperzine A by resolving (±)-huperzine A utilizing the principle that diastereomers have different solubilities in different solvents. Therefore, (−)-huperzine A of high purity can be obtained through a chiral resolution method. However, it has been found that the selection of a resolving agent and resolving solvent is highly important for production, and the reaction conditions should be strictly controlled in order to achieve the aim of this invention. Therefore, the present invention also provides optimized reaction conditions in order to achieve reaction conditions suitable for industrial production.

The screening process of the present invention is as follows.

This invention first prepared a series of huperzine A-chiral acid salts. The structures are confirmed by $^1$H NMR and TGA, and the physicochemical properties, like melting point and solubility, are also measured.

During the screening process, it was found that the formation rates of (−)-huperzine A-chiral acid salt and (+)-huperzine A-chiral acid salt are significantly different. (−)-Huperzine A can quickly form salt with D-dibenzoyl tartaric acid. Salts start to precipitate in one minute and salt formation is complete in 1 h. (+)-Huperzine A forms salt slowly with D-dibenzoyl tartaric acid. Salts start to precipitate in 10 minutes and salt formation is complete in 3 h. (−)-Huperzine A can quickly form salt with D-tartaric acid, with salts starting to precipitate in one hour and salt formation complete in 2 h. (+)-Huperzine A forms salt slowly with D-tartaric acid, with salts starting to precipitate in about 5 h and salt formation complete in 6 h.

The screening of resolving agents is as below.

TABLE 1

Comparison of resolving effect of different resolving agents

| Resolving agent | Yield | Optical purity |
| --- | --- | --- |
| D-dibenzoyl tartaric acid | 75%-85% | 95%-99.5% |
| D-tartaric acid | 50% | 95% |
| D-malic acid | 79% | 10% |
| D-mandelic acid | 50% | 10% |
| D-camphorsulfonic acid | 75% | 10% |

It was also found in the detailed experiments that when malic acid or camphor sulfonic acid is used to prepare huperzine A salts, the product cannot be precipitated completely, and is hard to purify, and the optical purity for the salt obtained is around 10%. When dibenzoyl tartaric acid is used, higher yield and optical purity can be obtained, and the product can be purified easily. Accordingly, the most preferable chiral acid in this invention is dibenzoyl tartaric acid, specifically, D-dibenzoyl tartaric acid.

During the optimization process, it is found that the solubilities of (−)-huperzine A and (+)-huperzine A are significantly different from one another, as shown in Tables 2 and 3.

TABLE 2

Comparison of solubility of huperzine A-dibenzoyl tartaric acid salts (temperature: 25° C., g/100 ml)

| | (−)-huperzine A-dibenzoyl tartaric acid salt | (+)-huperzine A-dibenzoyl tartaric acid salt |
| --- | --- | --- |
| Acetone | 0.07 | 0.02 |
| Water | 0.08 | 0.37 |
| Ethanol | 0.47 | 3.57 |

TABLE 3

Comparison of solubility of huperzine A tartaric acid salts (temperature: 25° C.)

| | (−)-huperzine A-tartaric acid salt | (+)-huperzine A-tartaric acid salt |
| --- | --- | --- |
| Acetone | 0.05 | 0.04 |
| Water | 68.95 | 5.00 |
| Ethanol | 2.74 | 1.47 |

Due to the significant differences in the rate of salt formation and solubility of salt, huperzine A can be resolved with high optical purity.

The optimization process of resolving solvent is as follows. Various common resolving solvents and mixed solvents with different ratios were studied and found to have significantly different resolving effects, as shown in Table 4.

TABLE 4

Comparison of resolving effect of different resolving solvents

| Resolving solvent | Yield | Optical purity |
|---|---|---|
| Acetone | 50%-55% | 95%-99.5% |
| Ethanol | 50%-60% | 95%-99.5% |
| Ethyl acetate | 60%-70% | 90% |
| DMF | 5%-10% | 80%-90% |
| DMSO | 5%-10% | 80%-90% |
| Acetone/water = 5/1 | 80% | 95% |
| Acetone/water = 3/1 | 75% | 98% |
| Acetone/water = 1/1 | 74% | 99.5% |
| Ethanol/water = 5/1 | 79% | 95% |
| Ethanol/water = 3/1 | 75% | 98% |
| Ethanol/water = 3/1 | 73% | 99% |
| Ethanol/water = 1/1 | 70% | 99.5% |

It was also found in the detailed experiments that the solvent has a great influence on the degree and the efficiency of salt formation between (±)-huperzine A and a chiral acid. When the salt formation occurs in various single solvents, the solubility of (±)-huperzine A is very poor, and the salt formation is incomplete, directly affecting the optical purity of the product. When aprotic solvents like DMF and DMSO are used, the precipitation of product is poor and the purification is difficult, leading to extremely low yields. The solvent in this invention can be selected from water, acetone, ethyl acetate, and ethanol as a single solvent, and can also be any mixture of the solvents above. The preferred solvent mixture is acetone-water or ethanol-water.

The detailed optimization process of the molar ratio of (±)-huperzine A/chiral acid is discussed as follows. A number of resolving agent/huperizin A ratios have been evaluated and found that the resolving effects of different ratios are significantly different, as shown in Table 5.

TABLE 5

Comparison of resolving effect of different ratios of huperzine A/resolving agent

| Molar ratio | Yield | Optical purity |
|---|---|---|
| 1:2 | 80% | 92% |
| 1:1.5 | 75% | 95% |
| 1:1 | 71% | 99% |
| 1:0.8 | 71% | 99.5% |
| 1:0.5 | 60% | 99.5% |

It was also found in the detailed experiments that the (±)-huperzine A/chiral acid ratio and the solvent has a great influence on the optical purity of products for chiral resolution. When the amount of chiral acid is decreased, the time of precipitation is longer and the yield is lower. When the amount of chiral acid exceeds a certain value, the optical purity of the obtained product is significantly lowered. The optimized molar ratio of (±)-huperzine A/chiral acid ranges from 1:0.5 to 1:2.

After optimization, the most preferable experimental method disclosed in this invention is discussed as follows. (±)-Huperzine A is suspended in acetone-water or ethanol-water, wherein the ratio of the acetone-water is 1:1 to 5:1 (v:v), and the ratio of ethanol-water is 1:1 to 5:1 (v:v). The molar ratio of (±)-huperzine A to chiral acid ranges from 1:0.5 to 1:2. After salt formation, the resulting salt is filtered, washed and then dried to give (−)-huperzine A-chiral acid salt. The salt is added to water and thoroughly mixed, wherein the weight ratio of the salt to water ranges from 1:2 to 1:8. Then, aqueous sodium hydroxide is used to adjust the pH value ranging from 9.0 to 9.3. Finally, the precipitated crystal is filtered to give a solid, which is then dried to give (−)-huperzine A. The yield of (−)-huperzine A is higher than 70% with the optical purity higher than 99.5%, and the chemical purity is higher than 99.5%.

Accordingly, the present invention provides (−)-huperzine A with high purity. By utilizing the method in this invention, pure (−)-huperzine A can be obtained with an optical purity higher than 99.5% and a chemical purity higher than 99.5%. The pure product exists in a form of crystal. This invention also provides a crystal of (−)-huperzine A, whose infrared spectrum and X-ray diffraction pattern are shown in the figures. The melting point of (−)-huperzine A crystal, which is white, is 222-224° C.

Since the method in this invention can obtain (−)-huperzine A in an industrial scale, and the method and preparation process have not been reported, this invention provides an intermediate compound during the preparation, e.g, huperzine A-chiral acid salts. The preferred huperzine A-chiral acid salts are huperzine A-dibenzoyl tartaric acid salt, huperzine A-tartaric acid salt, huperzine A-malic acid salt, huperzine A-mandelic acid salt, and huperzine A-camphorsulfonic acid salt.

Because these salts exist in the form of (±)-huperzine A-chiral acid salt as well as in the form of (−)-huperzine A-chiral acid salt, all these salts are included in this invention. The intermediate compound is selected from:

salt of (±)-Huperzine A and D-dibenzoyl tartaric acid,
salt of (±)-Huperzine A and D-tartaric acid,
salt of (±)-Huperzine A and D-malic acid,
salt of (±)-Huperzine A and D-mandelic acid,
salt of (±)-Huperzine A and D-camphor sulfonic acid,
salt of (−)-Huperzine A and D-dibenzoyl tartaric acid,
salt of (−)-Huperzine A and D-tartaric acid,
salt of (−)-Huperzine A and D-malic acid,
salt of (−)-Huperzine A and D-mandelic acid, and
salt of (−)-Huperzine A and D-camphor sulfonic acid.

In order to prove the presence of these obtained salts, the structure is verified as follows.

The NMR data of (−)-huperzine A-D-dibenzoyl tartaric acid salt is as follows:

$^1$H NMR (400 MHz, DMSO d6) δ 7.96 (d, J=7.6 Hz, 2H), 7.79 (d, J=9.6 Hz, 1H), 7.61-7.65 (m, 1H), 7.47-7.51 (m, 2H), 6.15 (d, J=9.6 Hz, 1H), 5.68 (s, 1H), 5.41-5.46 (m, 2H), 3.56 (s, 1H), 2.63-2.68 (m, 1H), 2.51-2.55 (m, 1H), 2.11-2.31 (m, 2H), 1.63 (d, J=6.4 Hz, 3H), 1.49 (s, 3H).

The NMR data of (−)-huperzine A-D-tartaric acid salt is as follows:

$^1$H NMR (400 MHz, D$_2$O) δ 7.87 (d, J=9.6 Hz, 1H), 6.63 (d, J=9.6 Hz, 1H), 5.63-5.64 (m, 1H), 5.51-5.56 (m, 1H), 4.51 (s, 2H), 3.88 (s, 1H), 3.04-3.10 (m, 1H), 2.79-2.84 (m, 1H), 2.68-2.72 (m, 1H), 2.53-2.57 (m, 1H), 1.82 (d, J=6.4 Hz, 3H), 1.65 (s, 3H).

The NMR data of (−)-huperzine A-D-camphorsulfonic acid salt is as follows:

$^1$H NMR (400 MHz, D$_2$O) δ 7.88 (d, J=9.6 Hz, 1H), 6.64 (d, J=9.6 Hz, 1H), 5.62-5.66 (m, 1H), 5.52-5.57 (m, 1H), 3.89 (s, 1H), 3.33-3.37 (m, 1H), 3.05-3.11 (m, 1H), 2.91-2.95 (m, 1H), 2.81-2.85 (m, 1H), 2.68-2.72 (m, 1H), 2.45-

2.57 (m, 3H), 2.21-2.23 (m, 1H), 2.07-2.14 (m, 2H), 1.83 (d, J=6.4 Hz, 3H), 1.66-1.74 (m, 4H), 1.48-1.54 (m, 1H), 1.11 (s, 3H), 0.90 (s, 3H).

The present invention also includes use of huperzine A-chiral acid salt for the preparation of (−)-huperzine A.

The present invention also includes pure (−)-huperzine A, which is prepared by the method of the present invention, with optical purity of more than 99.5% and chemical purity greater than 99.5%.

(−)-Huperzine A obtained by the method of the present invention has obvious advantages over existing technologies as follows.

(1) High Purity

The present invention provides pure (−)-huperzine A, which is characterized by its purity of greater than 99.5%, with the amount of the impurity (I) between 0.01% and 0.03%.

Impurity (I)

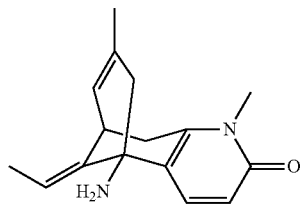

The purity of (−)-huperzine A prepared by the preferred method of the present invention is greater than 99.5%, further recrystallization step can achieve a purity greater than 99.8%, which is much higher than the quality standards of commercially available raw material of huperzine A and pharmacopoeia requirements of huperzine A.

(2) Consistent Quality and Clear Impurity Profile

In the present invention, detailed studies of the impurity profile have been carried out for multiple batches of the final product. The inventors of the present invention identified the impurity structure with content more than 0.005%; namely: WB0001, WB0002, WB0003, WB0004, WB0005 and WB0006. The structures are as follows:

WB0001

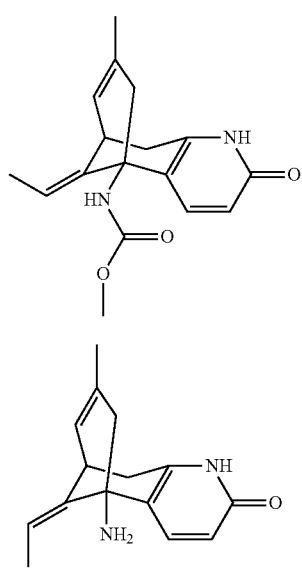

WB0002

WB0003

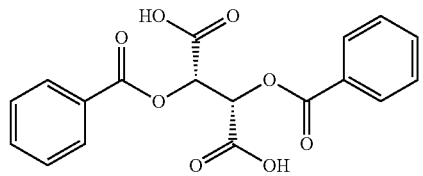

WB0004

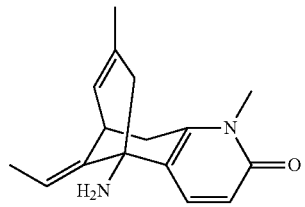

WB0005

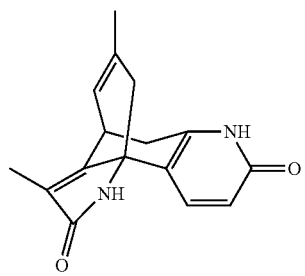

WB0006

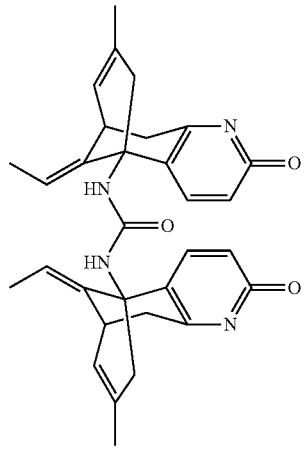

To this end, (−)-huperzine A provided by the present invention is further characterized that the total impurity amount of WB0001, WB0002, WB0003, WB0004, WB0005 and WB0006 is not more than 0.05%.

(3) Low Cost

Because the chiral resolution yield of the key step is increased, the cost of the raw material used in the present invention for the preparation of huperzine A is only one-third to one-half of that of other existing technologies, greatly reducing the medical cost for patients.

Since the quality of huperzine A produced by the present invention is much higher than pharmacopoeia standards and commercially available raw material of huperzine A, together with the low cost of large-scale production, consistent quality and clear impurity profile, these attributes fully comply with the requirements for the new generation of medicinal huperzine A raw material for the production of finished pharmaceutical products.

In view of this, the present invention also provides pharmaceutical formulations of (−)-huperzine A with the above-mentioned qualities. The pharmaceutical formulations of the present invention, wherein the (−)-huperzine A prepared by the method of the present invention may be combined with pharmaceutically acceptable inert carriers, and formulated for oral, parenteral or topical application. These pharmaceutical formulations can be solid, semisolid or liquid. For this purpose, these pharmaceutically acceptable inert carriers can be solid or liquid. The forms of pharmaceutical formulations include, but are not limited to, tablets, capsules, granules, powders, suppositories, transdermal, dripping pills, oral liquid, sprays and injections as well as a variety of slow and controlled release and fill buried dosage forms. When preparing solid or semi-solid pharmaceutical formulations, a solid carrier is generally used. Such solid carrier contains one or more of the substances preferably diluent, flavoring agents, solubilizers, lubricants, suspending agents, binders, bulking agents and the like, or encapsulating material. In the powder formulation, the carrier contains 5% to 70% of the micronized active ingredient. Examples of suitable solid carriers include polyethylene glycol 6000, polyethylene glycol 4000, polyethylene glycol 1500, polyoxyl stearate (40) ester, magnesium carbonate, magnesium stearate, talc, sugar, lactose, pectin, dextrin, starch, gelatin, tragacanth, methyl cellulose, sodium carboxymethyl cellulose, low boiling wax, cocoa butter and the like. Because of their ease of administration, dripping pills, tablets, powders and capsules represent the solid dosage forms for the most favorable absorption by oral administration.

Liquid formulations include solutions, suspensions and emulsions. For example, injectable formulations for parenteral administration may be in the form of a solution containing water or water mixed with ethanol or propylene glycol, in order to regulate the isotonic and pH value suitable for physiological conditions in the living body. Liquid preparations can also be made in the form of an aqueous solution of polyethylene glycol. Oral solution can be prepared by dissolving the active ingredient in water, followed by addition of suitable colorants, flavors, stabilizers and thickening agents. Aqueous suspension for oral administration can be prepared by dispersing the micronized active ingredients in viscous materials such as natural or synthetic gums, methylcellulose, sodium carboxymethyl cellulose and other known suspending agents.

For ease of administration and uniformity of dosage, it is particularly advantageous to prepare the aforementioned formulations in unit dosage forms. Formulations in unit dosage forms refer to a physically discrete unit suited as unitary dosages, and each unit contains a predetermined quantity of an active agent calculated to produce the desired therapeutic effect. Such unit dosage forms can be a packaged form, such as tablets, capsules, powder packed in small tubes or vials, and dripping pills or oral liquid packaged in a tube or bottle.

Although the amount of active ingredient contained in the unit dosage forms may vary, it is generally adjusted within a range of 30-200 μg according to the effectiveness of the active ingredient.

A preferred formulation of the present invention includes tablets, capsules, dripping pills, oral solution and solution for injection. They can be prepared by conventional pharmaceutical techniques, and can also be prepared by the method of the present invention designed by the present inventors, in order to achieve the best technical effect.

The preparation method designed by the present inventors is as follows.

The production method of the tablet is as follows.

A solution is prepared by dissolving (−)-huperzine A in 20-100 parts by weight of solvent, and then following the steps as shown below.

A) The solution is dispersed in 60-800 parts by weight of a matrix by spraying method, and then stirred thoroughly. Granules are prepared according to wet granulation, followed by drying and tableting. Or B) Solid dispersion is prepared by the solid dispersion method. A solution is added to 20-200 parts by weight of molten matrix materials, which is then cooled and pulverized to form the solid dispersion. Said solid dispersion uses a solution of (−)-huperzine A dissolved in a solvent, and then added to molten matrix materials, which are then stirred thoroughly, cooled and pulverized to form the homogenous solid dispersion. The solid dispersion was then added to 20-200 parts by weight of excipient matrix materials, and then stirred thoroughly. Granules are prepared according to wet granulation, followed by drying and tableting.

The solvent is selected from water, dilute hydrochloric acid, ethanol, glycerol, propylene glycol and acetone.

The excipient matrix is selected from polyethylene glycol 6000, polyethylene glycol 4000, polyethylene glycol 1500, polyoxyl stearate (40) ester, polyvinylpyrrolidone, polysorbate 80, xylitol, mannitol, lactose, sucrose, corn starch, dextrin, microcrystalline cellulose, talc, sodium bicarbonate, magnesium stearate, aluminum stearate, sodium stearate, insect wax, beeswax, stearyl alcohol, cetyl alcohol, hydroxypropyl methyl cellulose, ethyl cellulose, sodium hydroxypropyl cellulose, polyvinylpyrrolidone, gelatin, tragacanth, peach gum, gum arabic, alginic acid, chitin and glucosamine.

The production method of capsules is as follows.

A solution is prepared by dissolving (−)-huperzine A in a solvent, and then following the steps as shown below.

A) The solution is dispersed in 60-800 parts by weight of a matrix by spraying method, and then stirred thoroughly. Granules are prepared according to wet granulation, followed by drying and capsule filling.

B) Solid dispersion is prepared by the solid dispersion method. The (−)-huperzine A solution is added to 20-200 parts by weight of molten matrix materials, which are then cooled and pulverized to form the solid dispersion. Said solid dispersion uses a solution of (−)-huperzine A dissolved in a solvent, and then added to molten matrix materials, which are then stirred thoroughly, cooled and pulverized to form the homogenous solid dispersion. The solid dispersion was then added to 20-200 parts by weight of excipient matrix materials, and then stirred thoroughly. Granules are prepared according to wet granulation, followed by drying and filling into capsules.

The solvent is selected from dilute hydrochloric acid, ethanol, glycerol, propylene glycol and acetone.

The excipient matrix is selected from polyethylene glycol 6000, polyethylene glycol 4000, polyethylene glycol 1500, polyoxyl stearate (40) ester, polyvinylpyrrolidone, polysorbate 80, xylitol, mannitol, lactose, sucrose, corn starch, dextrin, microcrystalline cellulose, talc, sodium bicarbonate, magnesium stearate, aluminum stearate, sodium stearate, insect wax, beeswax, stearyl alcohol, cetyl alcohol, hydroxypropyl methyl cellulose, ethyl cellulose, sodium hydroxypropyl cellulose, polyvinylpyrrolidone, gelatin, tragacanth, peach gum, gum arabic, alginic acid, chitin and glucosamine.

The production method of dripping pill is as follows.

A solution is prepared by dissolving one part of (−)-huperzine A in 10-100 parts by weight of a solvent. The dripping pill is obtained by the method of dropwise addition of a dispersant. The method involves addition of the solution to 200-1500 parts by weight of a molten matrix, followed by stirring, dripping the melted mixture in a condensing agent, condensing into dripping pills, filtering the condensing agent and drying.

The solvent is selected from dilute hydrochloric acid, ethanol, glycerol and propylene glycol.

The matrix is selected from polyethylene glycol 6000, polyethylene glycol 4000, polyethylene glycol 1500, insect wax, sodium stearate, polyoxyl stearate (40) esters, polysorbate 80, xylitol, mannitol, lactose, sucrose, starch, dextrin, medicinal vegetable oil, glycerinated gelatin, tragacanth, peach gum, gum arabic, alginic acid, glucosamine.

The coolant is selected from dimethyl silicone oil, liquid paraffin, edible vegetable oil, ethanol and iced brine solution.

The production method of the solution for injection is as follows:

(−)-Huperzine A is mixed with an excipient; the excipient includes water soluble filler, pH regulator, injectable grade water, osmotic pressure regulator, etc, wherein the injection comprises lyophilized powder needles, small volume injection and large volume injection. The pH value under aqueous state is 5-9.

The water-soluble filler is selected from mannitol, dextran, sorbitol, polyethylene glycol, polysorbate 80, glucose, lactose or galactose. pH regulator is selected from citric acid, phosphoric acid, hydrochloric acid, other non-volatile acid, potassium hydroxide, sodium hydroxide, sodium carbonate, sodium bicarbonate and other physiologically acceptable organic or inorganic acids, bases and salts. Osmotic pressure regulator is selected sodium chloride and glucose.

The following are examples of solution for injection in the present invention.

(1) Lyophilized Injection

| (−)-Huperzine A | 0.05%-0.1% |
|---|---|
| Water soluble filler | 50%-90% |
| pH regulator | 0.01%-0.10% |
| Osmotic pressure regulator | 0.1%-0.5% |

(2) Small Capacity Injection

| (−)-Huperzine A | 0.05%-0.1% |
|---|---|
| pH regulator | 0.01%-0.05% |
| Sodium chloride | 0.1%-0.5% |
| Injectable grade water | 99.5%-99.8% |

(3) Large Capacity Injection

| (−)-Huperzine A | 0.05%-0.1% |
|---|---|
| pH regulator | 0.01%-0.05% |
| Sodium chloride | 0.1%-0.5% |
| Injectable grade water | 99.5%-99.8% |

Suitable amount of injectable grade water is added to a mixture of (−)-huperzine A, water soluble filler, and osmotic pressure regulator, then the pH is adjusted to 5-9 until complete dissolution, and water is added to the mark. 0.1-0.5% of activated carbon is added, with stirring at 20-50° C. for 10-60 minutes. After the activated carbon is removed, the filtrate is filtered with microporous membrane to remove bacteria. The sterilized filtrate is aliquoted to give injections.

Advantages of the present invention are as follows:

1) The final product has high purity with chemical purity of more than 99.5% and optical purity over 99.5%. The purity of the drug containing huperzine A in the existing market is lower than the product prepared by the method of the present invention.

2) The recovery yield of resolution is high, which is more than 70%, further ensuring cost advantages of the product prepared by the present invention.

3) The production cost is low, about one-third to one-half of reported synthetic routes; therefore, a very significant cost advantage and market competitiveness can be anticipated.

4) The resolution process of the present invention is simple. As the solvents and reagents used are environment-friendly, and the production processes do not require special environmental requirements, such as temperature and pressure, etc, the process is suitable for industrial production.

5) The products have high purity and quality, which meet a variety of production requirements with high purity standard.

In the prior reports, the high purity of (−)-huperzine A of more than 98% is limited to the laboratory method, which has high cost, and is limited to experimental research. It is impossible to achieve mass production for widespread use. The method of the present invention using relatively simple process to obtain high purity (−)-huperzine A has low cost and is more practical.

Comparing with the existing technology, the production cost of the present invention is greatly reduced. In particular, the use of conventional resolution methods significantly reduced the production cost. The relevant experimental data are as follows. According to another method in patent CN101130520, 98% (−)-huperzine A was obtained, but the cost is greatly increased to about 600 yuan/gram. The method of cost calculation is as follows: (±)-O-methyl huperzine A obtained by asymmetric synthesis, hydrolysis, Curtis and other steps costs about 160 yuan/gram. However, the resolution yield of (±)-O-methyl-huperzine A is only 16%, which directly leads to an increased cost of the final product to about 600 yuan/gram.

The present invention achieves 98% (−)-huperzine A, having white color, and mp: 222-224° C., and the cost is 400 yuan/gram. The method of cost calculation is as follows: Through the early step process optimization, it is easy to get kilogram scale of (±)-huperzine A, with a cost of about 150 yuan/gram. Further use of various resolution agents with cost less than 100 yuan/kg for resolution, and high recovery rate result in a product cost of about 400 yuan/gram.

The above cost calculation method was audited by accountant, demonstrating objectivity and fairness.

In addition, comparing the present invention to the existing technology, the product of the present invention has a high chemical purity and high optical purity, which cannot be achieved by repeated recrystallization in the reported methods.

DETAILED DESCRIPTION OF THE INVENTION

Figure 1:
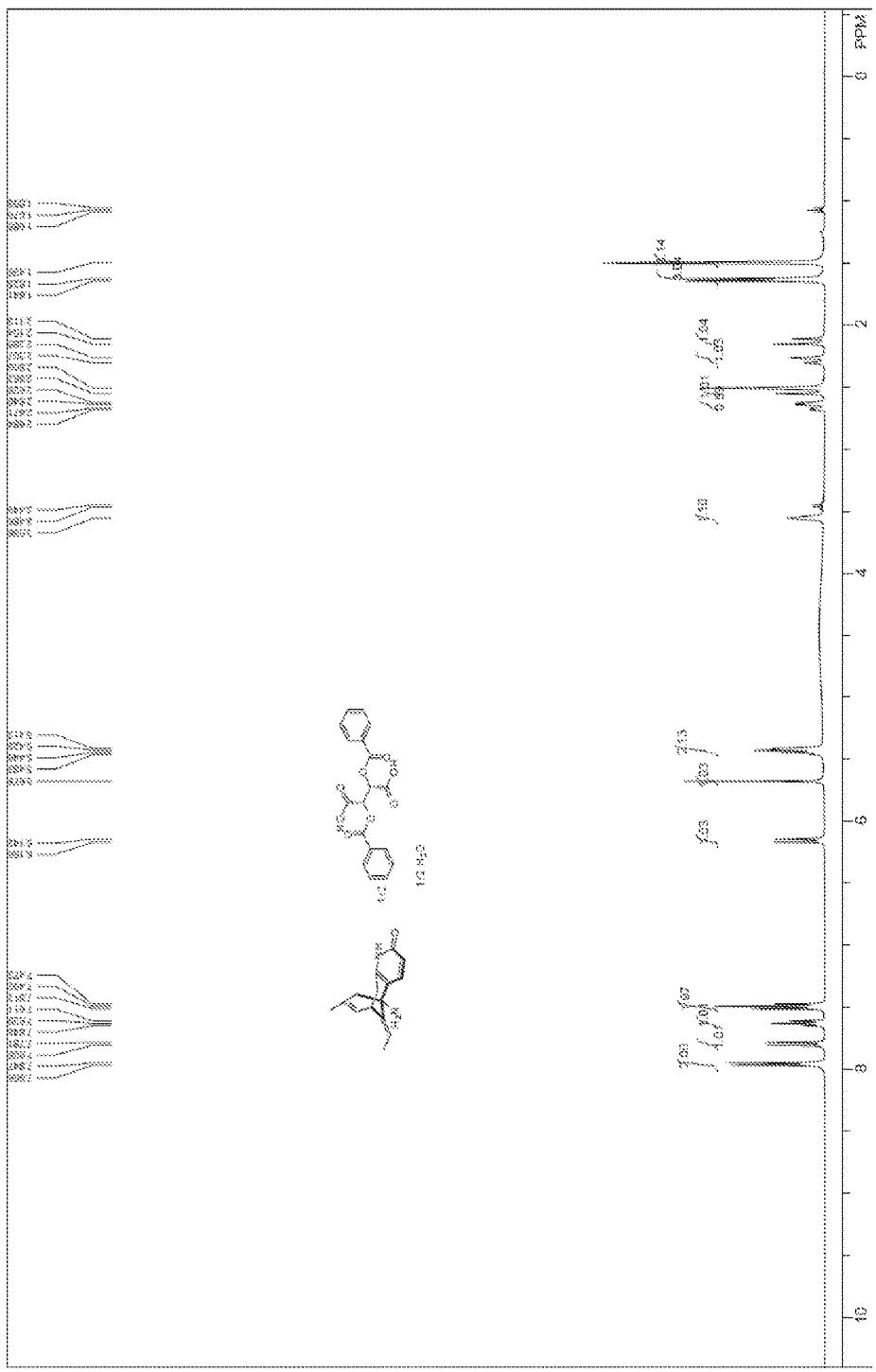
FIG. 1 shows the $^1$H-NMR spectrum of (−)-huperzine A-dibenzoyl tartaric acid salt.
Figure 2:
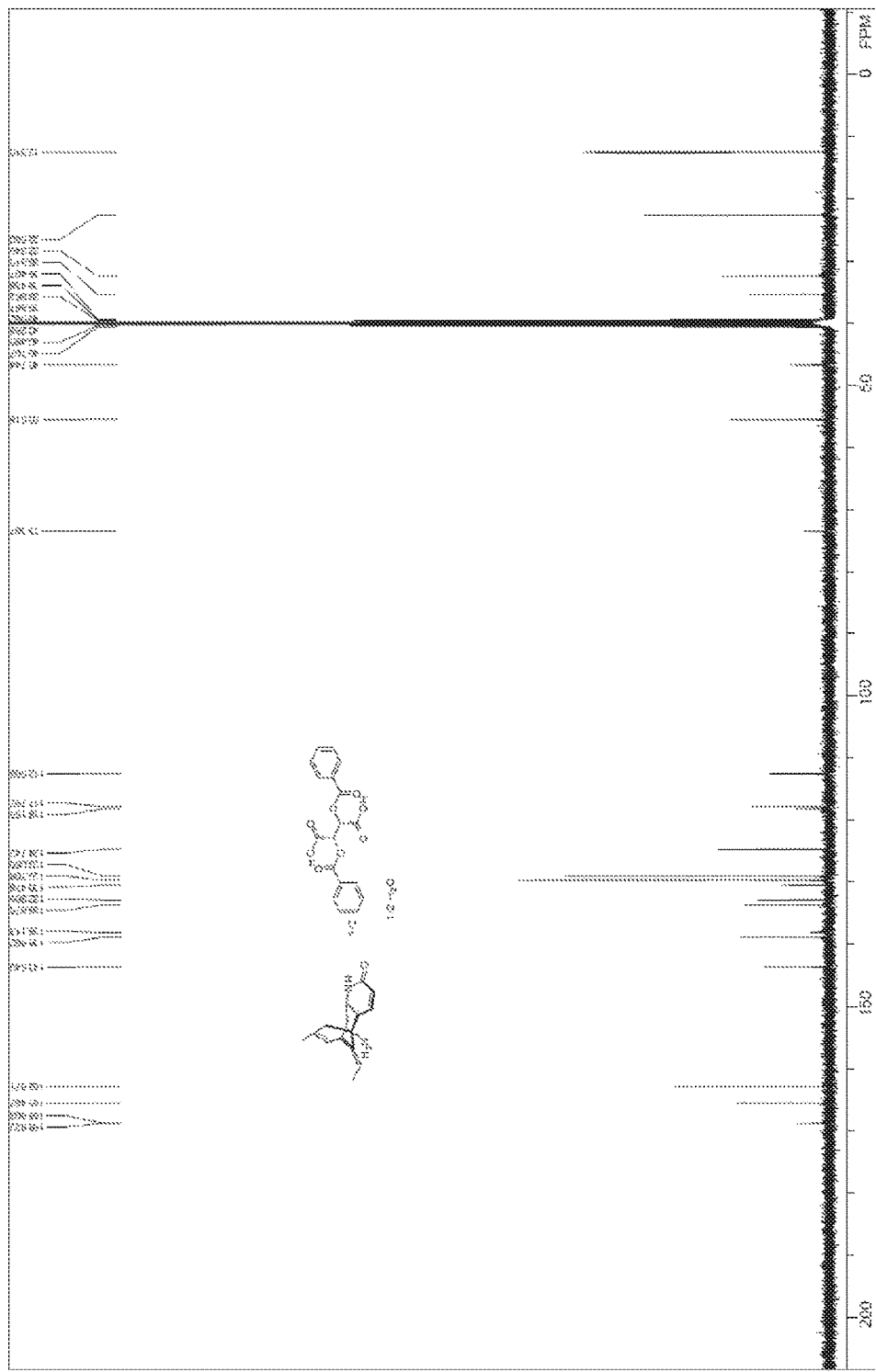
FIG. 2 shows the $^{13}$C-NMR spectrum of (−)-huperzine A-dibenzoyl tartaric acid salt.
Figure 3:
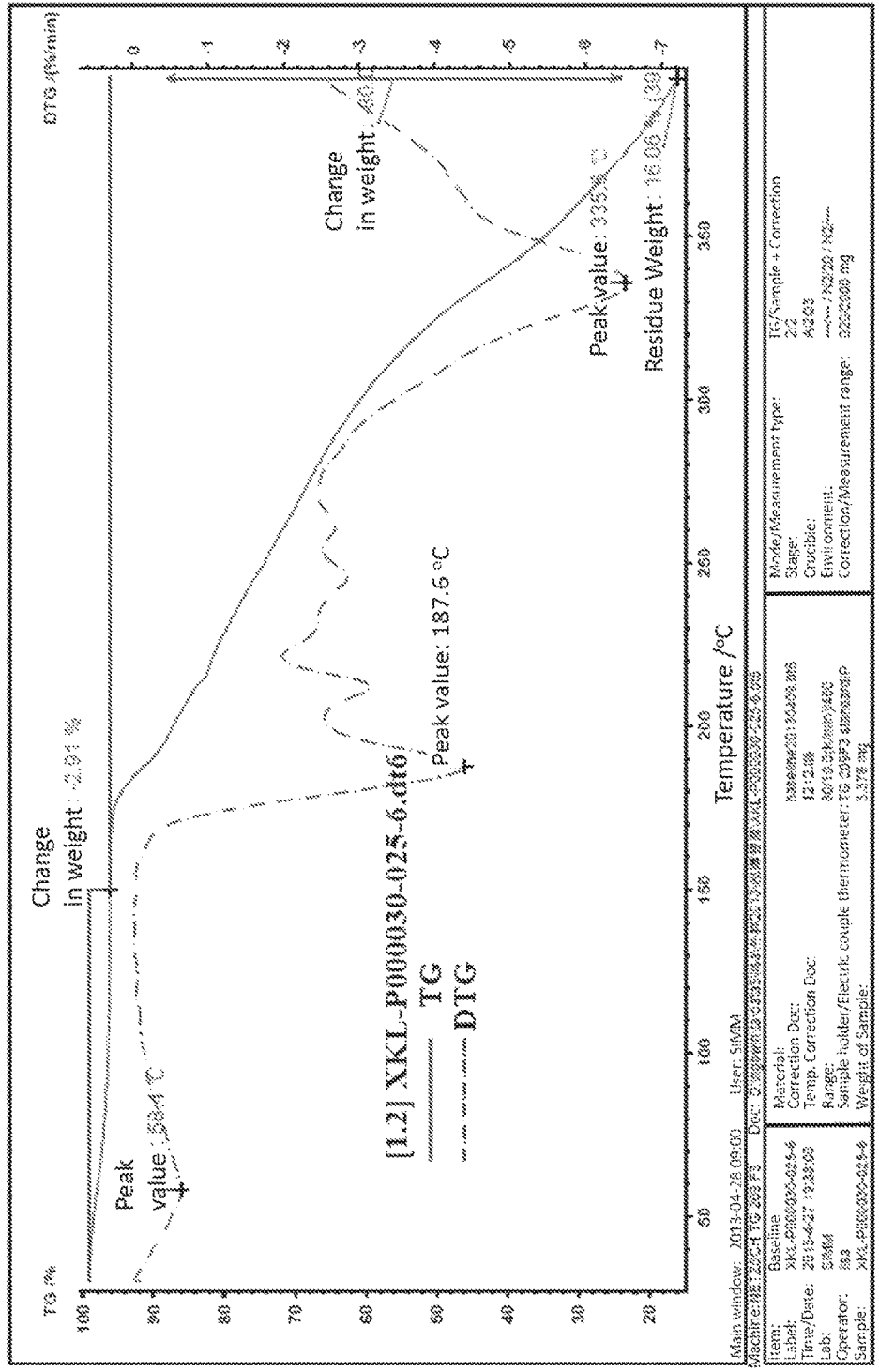
FIG. 3 shows the TGA spectrum of (−)-huperzine A-dibenzoyl tartaric acid salt.
Figure 4:
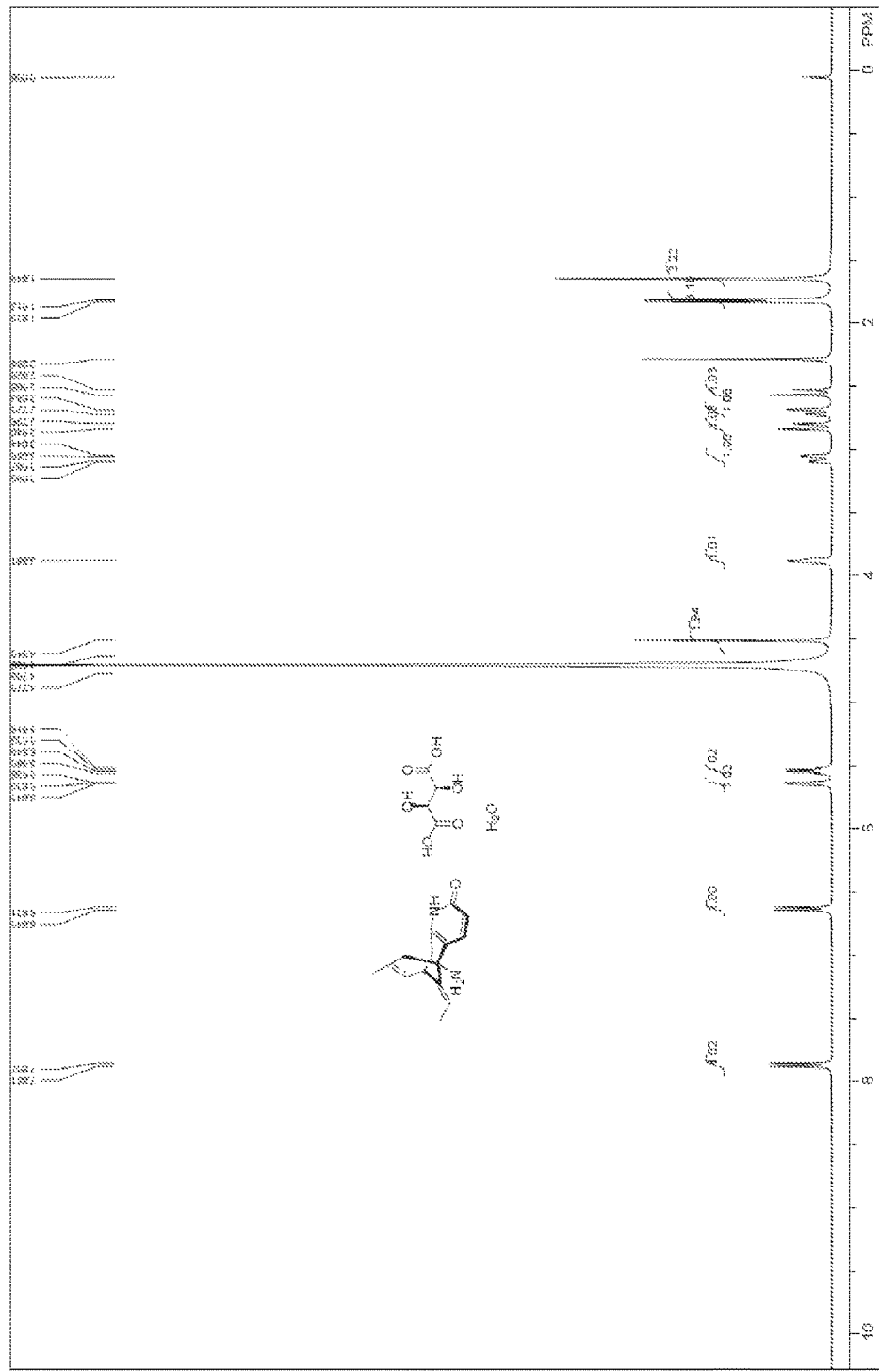
FIG. 4 shows the $^1$H-NMR spectrum of (−)-huperzine A-tartaric acid salt.
Figure 5:
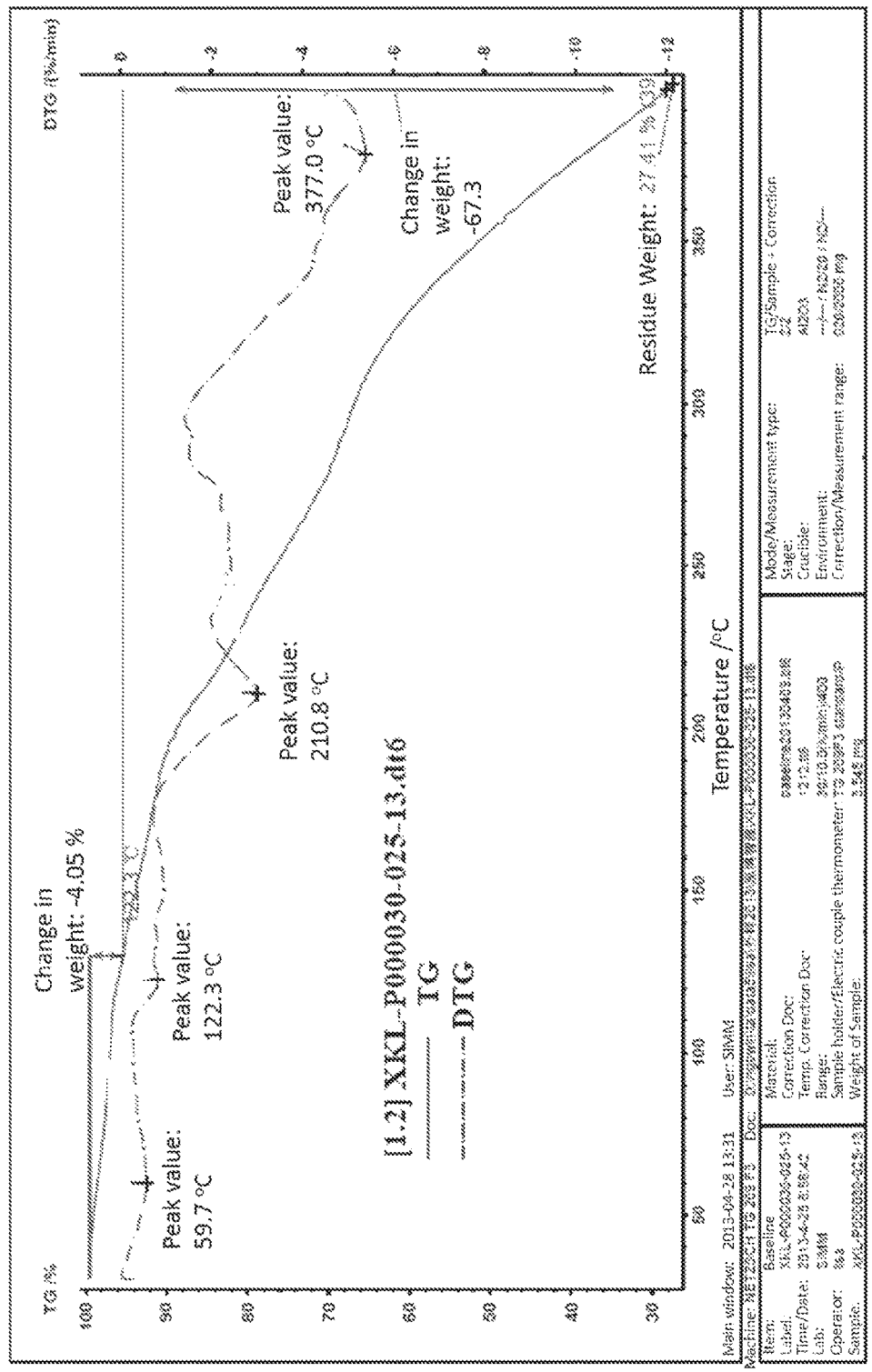
FIG. 5 shows the TGA spectrum of (−)-huperzine A-tartaric acid salt.
Figure 6:
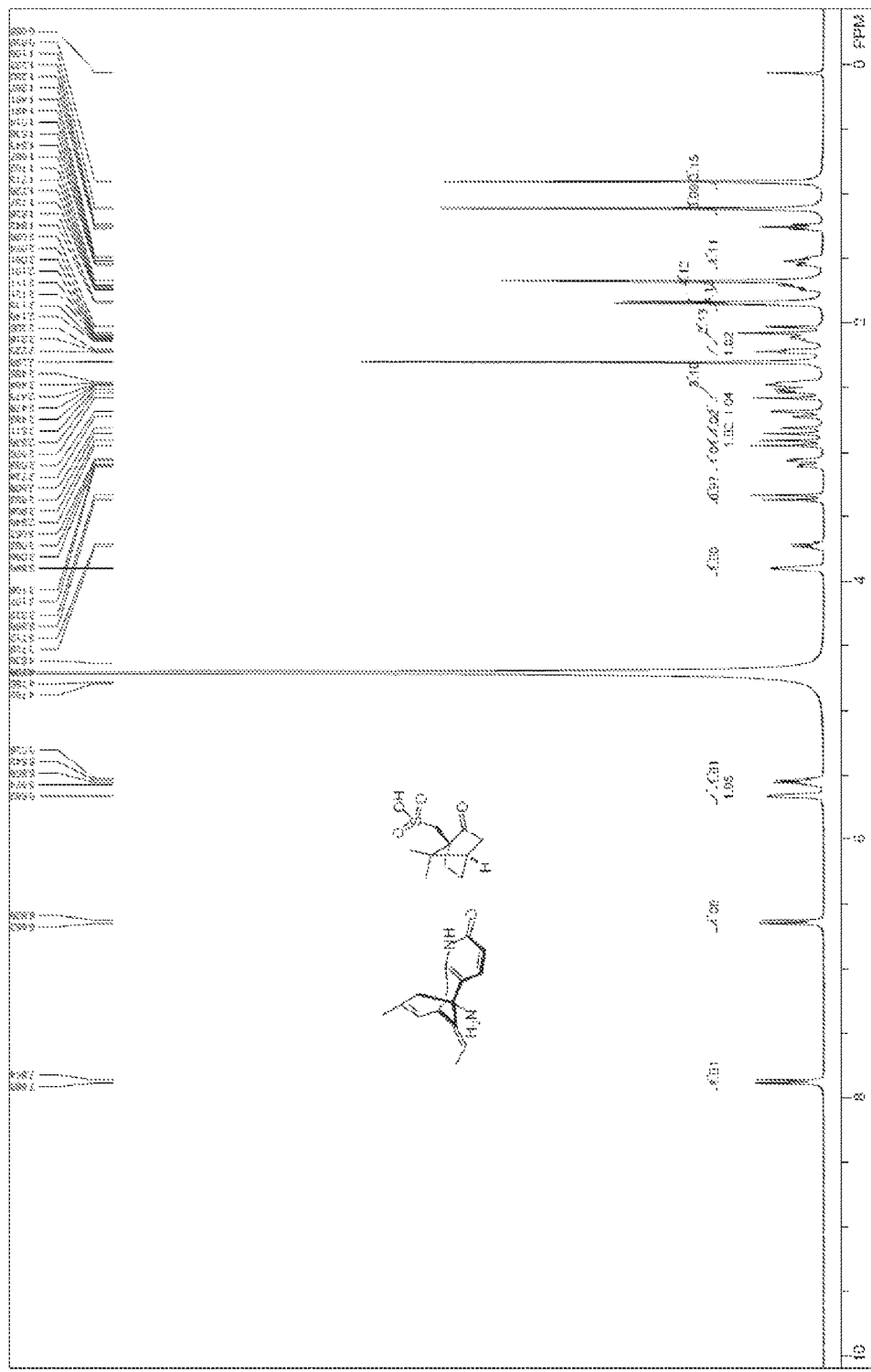
FIG. 6 shows the $^1$H-NMR spectrum of (−)-huperzine A-tartaric acid salt.
Figure 7:
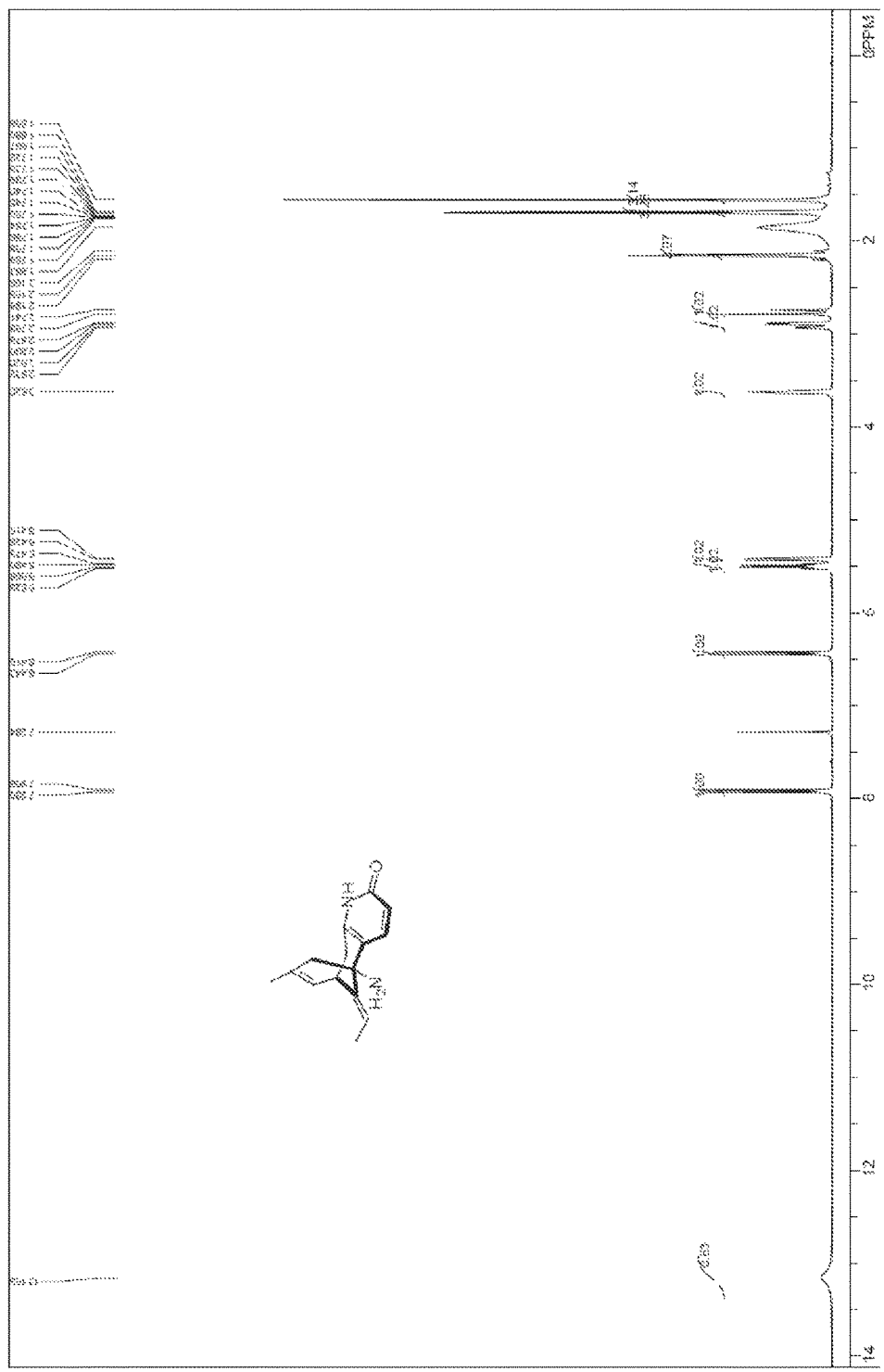
FIG. 7 shows the $^1$H-NMR spectrum of (−)-huperzine A.
Figure 8:
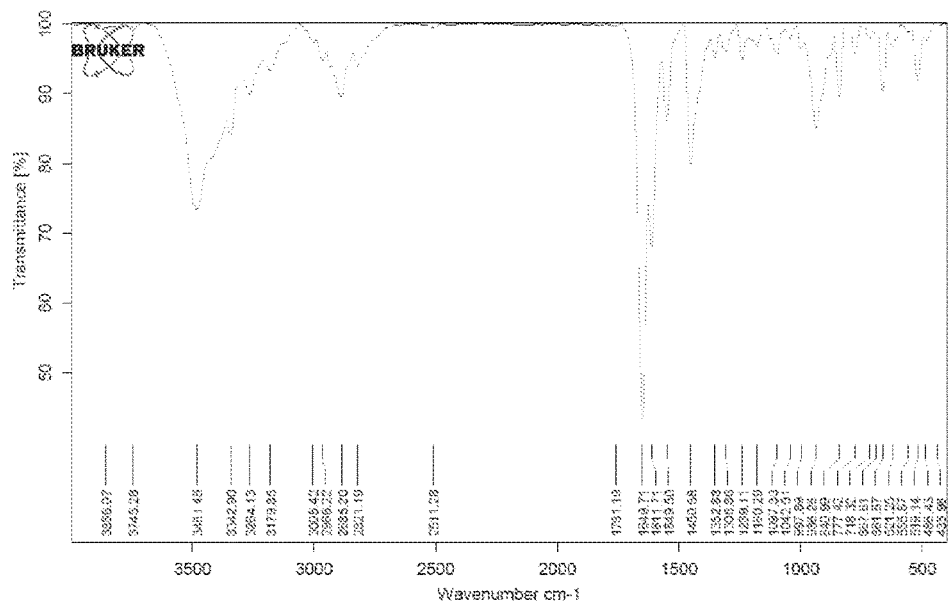
FIG. 8 shows the IR spectrum of (−)-huperzine A.
Figure 9:
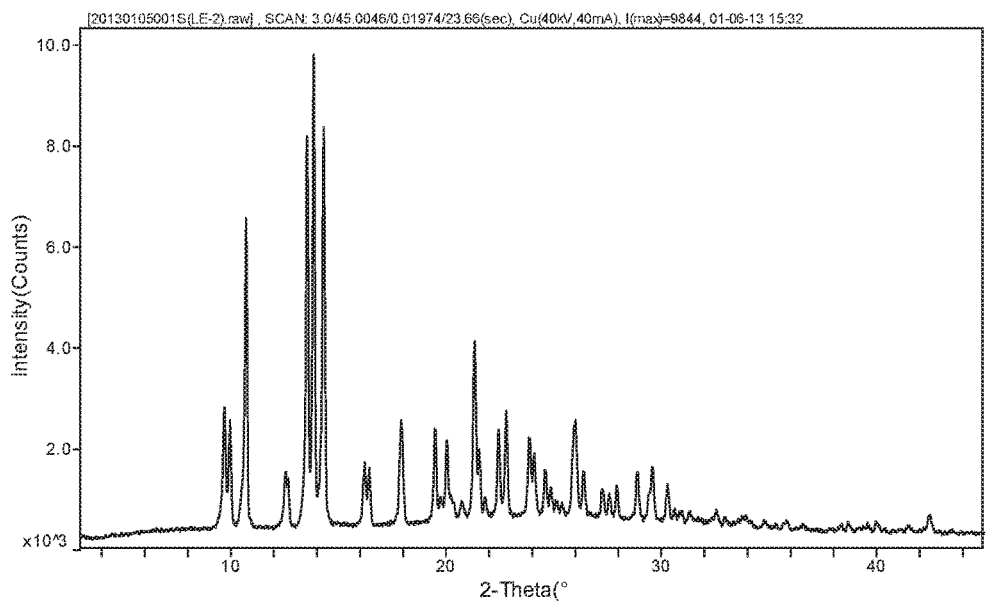
FIG. 9 shows the X-ray spectrum of (−)-huperzine A derivative X-ray spectrum.
Figure 10:
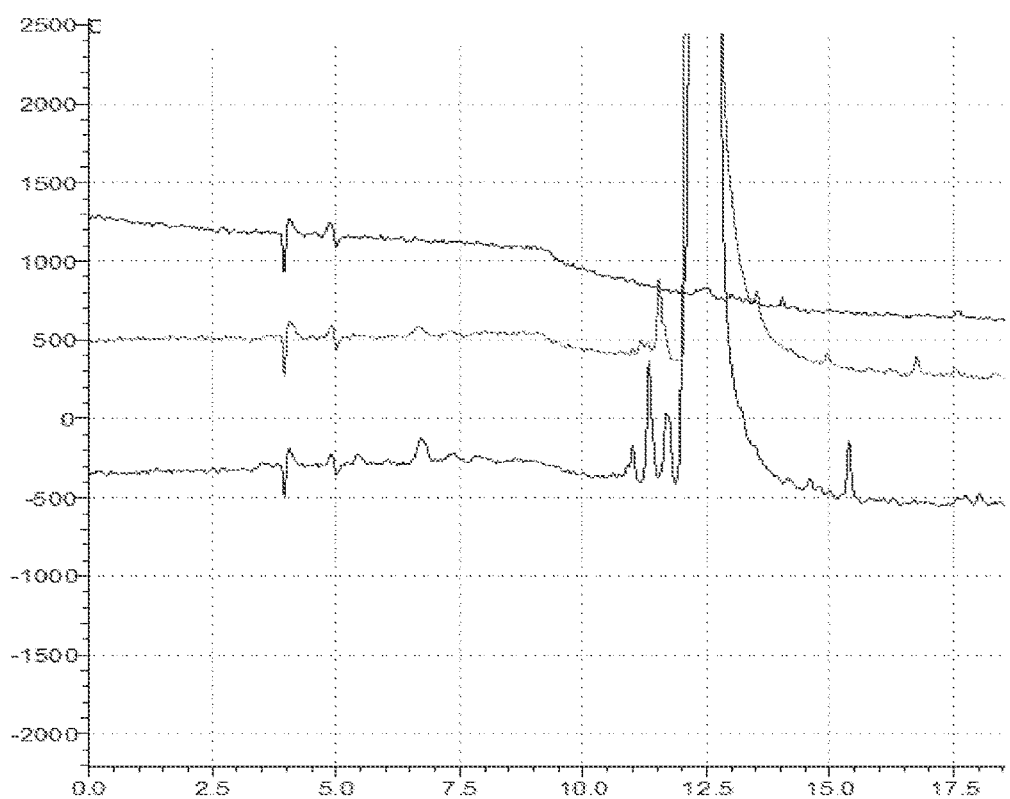
FIG. 10 is a HPLC chart comparing (−)-huperzine A obtained by the present invention and commercially available (−)-huperzine A. From top to bottom: Solvent blank; Sample of the present invention; Commercially available sample.

The following examples are used to further illustrate this invention, but are not meant to limit the scope of this invention.

Example 1

Preparation of (−)-huperzine A-D-dibenzoyl tartaric acid salt.

7.3 g of (±)-huperzine A was suspended in acetone-water with a ratio of 1:1 (v/v). 8.9 g of D-(−)-dibenzoyl tartaric acid was added at 20° C. After stirring for 1 h, the resulting salt was filtered to obtain a solid which was then recrystallized from anhydrous ethanol to give 8.5 g of (−)-huperzine A-D-dibenzoyl tartaric acid salt.

Yield: 82%, HPLC purity: 99% (310 nm), optical purity: 99.5%, m.p.: 175-177° C.

$^1$H NMR (400 MHz, DMSO d6) δ 7.96 (d, J=7.6 Hz, 2H), 7.79 (d, J=9.6 Hz, 1H), 7.61-7.65 (m, 1H), 7.47-7.51 (m, 2H), 6.15 (d, J=9.6 Hz, 1H), 5.68 (s, 1H), 5.41-5.46 (m, 2H), 3.56 (s, 1H), 2.63-2.68 (m, 1H), 2.51-2.55 (m, 1H), 2.11-2.31 (m, 2H), 1.63 (d, J=6.4 Hz, 3H), 1.49 (s, 3H).

Example 2

Preparation of (−)-huperzine A.

8.5 g of (−)-huperzine A-D-dibenzoyl tartaric acid salt was added into 42.5 ml of water. A solution of 40% sodium hydroxide was used to adjust the pH value to 9.0-9.3. The suspension was stirred for 1 h and then filtered. The solid was washed with 10 ml of water and recrystallized from 95% ethanol to give 3.6 g of (−)-huperzine A after drying under vacuum.

Yield: 74%, HPLC purity: 99.6% (310 nm), optical purity: 99.5%, m.p.: 217-219° C.

$^1$H NMR (400 MHz, CDCl$_3$) δ 13.16 (br, 1H), 7.92 (d, J=9.6 Hz, 1H), 6.43 (d, J=9.6 Hz, 1H), 5.47-5.52 (m, 1H), 5.41-5.43 (m, 1H), 3.62 (s, 1H), 2.88-2.93 (m, 1H), 2.74-2.78 (m, 1H), 2.11-2.19 (m, 2H), 1.63 (d, J=6.8 Hz, 3H), 1.56 (s, 3H).

Example 3

Preparation of (−)-huperzine A-D-tartaric acid salt.

6 g of (±)-huperzine A was suspended in acetone-water with a ratio of 1:1 (v:v). 3.1 g of D-tartaric acid was added at 20° C. After stirring for 1 h, the resulting salt was filtered to obtain a solid which was then recrystallized from anhydrous ethanol to give 4 g of (−)-huperzine A-D-tartaric acid salt.

Yield: 51%, HPLC purity: 98% (310 nm), optical purity: 95%, m.p.: 182-185° C.

$^1$H NMR (400 MHz, D$_2$O) δ 7.87 (d, J=9.6 Hz, 1H), 6.63 (d, J=9.6 Hz, 1H), 5.63-5.64 (m, 1H), 5.51-5.56 (m, 1H), 4.51 (s, 2H), 3.88 (s, 1H), 3.04-3.10 (m, 1H), 2.79-2.84 (m, 1H), 2.68-2.72 (m, 1H), 2.53-2.57 (m, 1H), 1.82 (d, J=6.4 Hz, 3H), 1.65 (s, 3H).

Example 4

The preparation of (−)-huperzine A-D-(+)-malic acid salt.

1 g of (±)-huperzine A was suspended in acetone-water with a ratio of 1:1 (v:v). 0.45 g of D-(+)-malic acid was added at 20° C. After stirring for 1 h, the resulting salt was filtered to obtain a solid which was then recrystallized from anhydrous ethanol to give 1 g of (−)-huperzine A-D-(+)-malic acid salt.

Yield: 79%, HPLC purity: 98% (310 nm), optical purity: 10%.

Example 5

The preparation of (−)-huperzine A-D-(+)-camphor sulfonic acid salt.

1 g of (±)-huperzine A was suspended in acetone-water with a ratio of 1:1 (v:v). 0.78 g of D-(+)-camphor sulfonic acid was added at 20° C. After stirring for 1 h, the resulting salt was filtered to obtain a solid which was then recrystallized from anhydrous ethanol to give 1.2 g of (−)-huperzine A-D-(+)-camphor sulfonic acid salt.

Yield: 75%, HPLC purity: 98% (310 nm), optical purity: 10%.

$^1$H NMR (400 MHz, D$_2$O) δ 7.88 (d, J=9.6 Hz, 1H), 6.64 (d, J=9.6 Hz, 1H), 5.62-5.66 (m, 1H), 5.52-5.57 (m, 1H), 4.51 (s, 2H), 3.89 (s, 1H), 3.33-3.37 (m, 1H), 3.05-3.11 (m, 1H), 2.91-2.95 (m, 1H), 2.81-2.85 (m, 1H), 2.68-2.72 (m, 1H), 2.45-2.57 (m, 3H), 1.48-1.54 (m, 1H), 0.90 (s, 3H).

Example 6

7.3 g of (±)-huperzine A was suspended in acetone-water with a ratio of 5:1 (v:v). 8.9 g of D-(−)-dibenzoyl tartaric acid was added at 20° C. After stirring for 1 h, the resulting salt was filtered to obtain a solid which was then recrystallized from anhydrous ethanol. A solution of 40% sodium hydroxide was used to adjust the pH value to 9.0-9.3 After stirring for 1 h, the suspension was filtered and the solid was washed with 10 ml of water. The solid was recrystallized from 95% ethanol, and then dried under vacuum to give (−)-huperzine A. Product obtained: 4.8 g, HPLC purity: 99.5% (310 nm), optical purity: 99.5%.

Example 7

7.3 g of (±)-huperzine A was suspended in acetone-water with a ratio of 3:1 (v:v). 8.9 g of D-(−)-dibenzoyl tartaric acid was added at 20° C. After stirring for 1 h, the resulting salt was filtered to obtain a solid which was then recrystallized from anhydrous ethanol. A solution of 40% sodium hydroxide was used to adjust the pH value to 9.0-9.3. After stirring for 1 h, the suspension was filtered and the solid was washed with 10 ml of water. The solid was recrystallized from 95% ethanol, and then dried under vacuum to give (−)-huperzine A. Product obtained: 4.5 g, HPLC purity: 99.7% (310 nm), optical purity: 99.5%.

Example 8

7.3 g of (±)-huperzine A was suspended in acetone-water with a ratio of 1:1 (v:v). 8.9 g of D-(−)-dibenzoyl tartaric acid was added at 20° C. After stirring for 1 h, the resulting salt was filtered to obtain a solid which was then recrystallized from anhydrous ethanol. A solution of 40% sodium hydroxide was used to adjust the pH value to 9.0-9.3. After stirring for 1 h, the suspension was filtered and the solid was washed with 10 ml of water. The solid was recrystallized from 95% ethanol, and then dried under vacuum to give (−)-huperzine A. Product obtained: 4.4 g, HPLC purity: 99.8% (310 nm), optical purity: 99.5%.

Example 9

7.3 g of (±)-huperzine A was suspended acetone-water with a ratio of 1:1 (v:v). 17.8 g of D-(−)-dibenzoyl tartaric acid was added at 20° C. After stirring for 1 h, the resulting salt was filtered to obtain a solid which was then recrystallized from anhydrous ethanol. A solution of 40% sodium hydroxide was used to adjust the pH value to 10.0-10.3. After stirring for 1 h, the suspension was filtered and the solid was washed with 10 ml of water. The solid was recrystallized from 95% ethanol, and then dried under vacuum to give (−)-huperzine A. Product obtained: 5.0 g, HPLC purity: 99.5% (310 nm), optical purity: 99.5%.

Example 10

7.3 g of (±)-huperzine A was suspended in acetone-water with a ratio of 1:1 (v:v). 13.4 g of D-(−)-dibenzoyl tartaric acid was added at 20° C. After stirring for 1 h, the resulting salt was filtered to obtain a solid which was then recrystallized from anhydrous ethanol. A solution of 40% sodium hydroxide was used to adjust the pH value to 10.0-10.3. After stirring for 1 h, the suspension was filtered and the solid was washed with 10 ml of water. The solid was recrystallized from 95% ethanol, and then dried under vacuum to give (−)-huperzine A. Product obtained: 4.8 g, HPLC purity: 99.5% (310 nm), optical purity: 99.5%.

Example 11

7.3 g of (±)-huperzine A was suspended in acetone-water with a ratio of 1:1 (v:v). 7.1 g of D-(−)-dibenzoyl tartaric acid was added at 20° C. After stirring for 1 h, the resulting salt was filtered to obtain a solid which was then recrystallized from anhydrous ethanol. A solution of 40% sodium hydroxide was used to adjust the pH value to 9.0-9.3. After stirring for 1 h, the suspension was filtered and the solid was washed with 10 ml of water. The solid was recrystallized from 95% ethanol, and then dried under vacuum to give (−)-huperzine A. Product obtained: 4.2 g, HPLC purity: 99.8% (310 nm), optical purity: 99.5%.

Example 12

7.3 g of (±)-huperzine A was suspended in acetone-water with a ratio of 1:1 (v:v). 4.45 g of D-(−)-dibenzoyl tartaric acid is added at 20° C. After stirring for 1 h, the resulting salt was filtered to obtain a solid which was then recrystallized from anhydrous ethanol. A solution of 40% sodium hydroxide was used to adjust the pH value to 9.0-9.3. After stirring for 1 h, the suspension was filtered and the solid was washed with 10 ml of water. The solid was recrystallized from 95% ethanol, and then dried under vacuum to give (−)-huperzine A. Product obtained: 3.5 g, HPLC purity: 99.8% (310 nm), optical purity: 99.5%.

Example 13

7 g of (±)-huperzine A was suspended in ethanol. 8.6 g of D-(−)-dibenzoyl tartaric acid was added at 40° C. After stirring for 1 h, the resulting salt was filtered to obtain a solid which was then recrystallized from anhydrous ethanol. A solution of 40% sodium hydroxide was used to adjust the pH value to 9.0-9.3. After stirring for 1 h, the suspension was filtered and the solid was washed with 10 ml of water. The solid was recrystallized from 95% ethanol, and then dried under vacuum to give (−)-huperzine A.

Product obtained: 3.0 g, HPLC purity: 99.9% (310 nm), optical purity: 99.5%.

Example 14

7 g of (±)-huperzine A was suspended in ethanol-water with a ratio of 1:1 (v/v). 8.6 g of D-(−)-dibenzoyl tartaric acid was added at 20° C. After stirring for 1 h, the resulting salt was filtered to obtain a solid which was then recrystallized from anhydrous ethanol. A solution of 40% sodium hydroxide was used to adjust the pH value to 9.0-9.3. After stirring for 1 h, the suspension was filtered and the solid was washed with 10 ml of water. The solid was recrystallized from 95% ethanol, and then dried under vacuum to give (−)-huperzine A. Product obtained: 4.0 g, HPLC purity: 99.7% (310 nm), optical purity: 99.6%.

Example 15

7 g of (±)-huperzine A was suspended in ethanol-water with a ratio of 5:1 (v/v). 8.6 g of D-(−)-dibenzoyl tartaric acid was added at 20° C. After stirring for 1 h, the resulting salt was filtered to obtain a solid which was then recrystallized from anhydrous ethanol. A solution of 40% sodium hydroxide was used to adjust the pH value to 9.0-9.3. After stirring for 1 h, the suspension was filtered and the solid was washed with 10 ml of water. The solid was recrystallized from 95% ethanol, and then dried under vacuum to give (−)-huperzine A. Product obtained: 4.5 g, HPLC purity: 99.5% (310 nm), optical purity: 99.5%.

Example 16

7 g of (±)-huperzine A was suspended in ethanol-water with a ratio of 3:1 (v/v). 8.6 g of D-(−)-dibenzoyl tartaric acid was added at 20° C. After stirring for 1 h, the resulting salt was filtered to obtain a solid which was then recrystallized from anhydrous ethanol. A solution of 40% sodium hydroxide was used to adjust the pH value to 9.0-9.3. After stirring for 1 h, the suspension was filtered and the solid was washed with 10 ml of water. The solid was recrystallized from 95% ethanol, and then dried under vacuum to give (−)-huperzine A. Product obtained: 4.3 g, HPLC purity: 99.5% (310 nm), optical purity: 99.5%.

Example 17

7 g of (±)-huperzine A was suspended in ethanol-water with a ratio of 2:1 (v/v). 8.6 g of D-(−)-dibenzoyl tartaric acid was added at 20° C. After stirring for 1 h, the resulting salt was filtered to obtain a solid which was then recrystallized from anhydrous ethanol. A solution of 40% sodium hydroxide was used to adjust the pH value to 10.0-10.3. After stirring for 1 h, the suspension was filtered and the solid was washed with 10 ml of water. The solid was recrystallized from 95% ethanol, and then dried under vacuum to give (−)-huperzine A. Product obtained: 4.2 g, HPLC purity: 99.5% (310 nm), optical purity: 99.5%.

Example 18

Example of huperzine A tablets is as follows:
Formulation:

| | |
|---|---|
| (−)-Huperzine A | 0.05 g |
| Lactose | 20.0 g |
| Starch | 40.0 g |
| Hydroxypropyl cellulose | 2.0 g |
| 10% polyvinyl pyrrolidone | Suitable amount |
| Magnesium stearate | 0.5 g |
| Dilute hydrochloric acid, Ethanol | Suitable amount |

Preparation method: Huperzine A was completely dissolved in the solvent, and then stirred thoroughly to form a dispersion of (−)-huperzine A, which was added to the mixed excipients by spraying method, followed by granulation with 20-mesh sieve and then dried. Magnesium stearate was added and the mixture was mixed homogeneously and then compressed into 1000 tablets.

Example 19

Example of huperzine A oral disintegrating tablet is as follows:
Formulation:

| | |
|---|---|
| (−)-Huperzine A | 0.05 g |
| Crosslinked sodium carboxymethyl cellulose | 3.0 g |
| Methylcellulose | 1.0 g |
| Citric acid | 0.5 g |
| Mannitol | 40 g |
| Aspartame | 0.5 g |
| Magnesium stearate | 1 g |
| Polysorbate 80 | 0.1 g |
| Dilute hydrochloric acid, ethanol | 20 ml |
| 1000 tablets prepared | |

Preparation method: Huperzine A was completely dissolved in the solvent and polysorbate 80 was added. The solution was stirred thoroughly to form dispersion of (−)-huperzine A, which was then added to the homogeneously mixed excipients of crosslinked sodium carboxymethyl cellulose, methyl cellulose, citric acid, mannitol and aspartame by spraying method. The mixture was homogeneously mixed by stirring, followed by addition of magnesium stearate. The mixture was mixed homogeneously and then compressed into tablets.

Example 20

Example of huperzine A capsules is as follows:
Formulation:

| | |
|---|---|
| (−)-Huperzine A | 0.05 g |
| Lactose | 40.0 g |
| Starch | 60.0 g |
| Hydroxypropyl cellulose | 2.0 g |
| 10% polyvinyl pyrrolidone | Suitable amount |
| Dilute hydrochloric acid, ethanol | Suitable amount |

Huperzine A was completely dissolved in the solvent to form a solution. The excipients above were added, and then stirred homogeneously. After granulation according to wet granulation method, the granules were sieved and dried. After the addition of microcrystalline cellulose, the mixture was assembled into 1000 capsules.

Example 21

Example of huperzine A capsules is as follows:
Formulation:

| | |
|---|---|
| (−)-Huperzine A | 0.05 g |
| Lactose | 20.0 g |
| Starch | 60.0 g |
| Microcrystalline cellulose | Suitable amount |
| 10% polyvinyl pyrrolidone | Suitable amount |
| Dilute hydrochloric acid, ethanol | Suitable amount |

Huperzine A was completely dissolved in the solvent to form a solution. The ingredients above were added, and then stirred homogeneously. After granulation according to the wet granulation method, the granules were sieved and dried. After the addition of microcrystalline cellulose, the mixture was assembled into 1000 capsules.

Example 22

Example of huperzine A capsules is as follows:
Formulation:

| | |
|---|---|
| (−)-Huperzine A | 0.10 g |
| Lactose | 50.0 g |
| Starch | 40.0 g |
| Hydroxypropyl cellulose | 4.0 g |
| 10% polyvinyl pyrrolidone | Suitable amount |
| Microcrystalline cellulose | Suitable amount |
| Dilute hydrochloric acid, ethanol | Suitable amount |

Huperzine A was completely dissolved in the solvent to form a solution. The ingredients above were added, and stirred homogeneously. After granulation according to the wet granulation method, the granules were sieved and dried. After the addition of microcrystalline cellulose, the mixture was assembled into 1000 capsules.

Example 23

Example of huperzine A dripping pills is as follows:
Formulation:

| | |
|---|---|
| (−)-Huperzine A | 0.05 g |
| Polyethylene glycol 4000 | 60.0 g |
| Dilute hydrochloric acid, ethanol | Suitable amount |

Huperzine A was completely dissolved in the solvent to form a solution. 1000 of dripping pills were obtained by addition of the above ingredients to form a molten matrix, followed by stirring, dripping the melted mixture in liquid wax or dimethyl silicone oil at 5-10° C., removing the oil and drying.

Example 24

Formulation:

| | |
|---|---|
| (−)-Huperzine A | 0.05 g |
| Polyethylene glycol 6000 | 60.0 g |
| Dilute hydrochloric acid, ethanol | Suitable amount |

Huperzine A was homogeneously dissolved in a proper amount of solvent, the molten polyethylene glycol 6000 was added and then mixed at 60-90° C. After the molten mixture was homogeneously mixed by stirring, it was transferred to the dripping container of a dripping machine, and then liquid wax or methyl silicone oil was added at 5-17° C. The dripping pills were moved out of the container, and liquid wax or methyl silicone oil was then removed. The dripping pills were screened and dried to obtain 1000 pills (weight per pill: 50-60 mg).

Example 25

Preparation method of lyophilized injection dosages is as follows.

| | |
|---|---|
| (−)-Huperzine A | 0.05% |
| Mannitol | 50% |
| Sodium chloride | 0.5% |

The rest is injectable grade water. (Each unit bottle contains 30-200 μg of (−)-huperzine A.)

A proper amount of injectable grade water was added to the above excipients. The pH was adjusted to 6-7 until complete dissolution. Water was added until it reached the mark and 0.1-0.5% of activated charcoal was added, followed by stirring for 10-60 min at 20-50° C. The activated charcoal was removed. The solution was filtered through microporous membrane to remove bacteria. The filtrate was aliquoted and lyophilized to give loose white lumps. The lyophilized injection dosages were obtained upon sealing.

Example 26

Preparation method of lyophilized injection dosages with low volume is as follows.

| | |
|---|---|
| (−)-Huperzine A | 0.05% |
| Sodium chloride | 0.5% |

The rest is injectable grade water. (Each unit bottle contains 30-200 μg of (−)-Huperzine A.)

A proper amount of injectable grade water was added into the above excipients. The pH was adjusted to 5-7 until complete dissolution. Water was added until it reached the mark and 0.1-0.5% of activated charcoal was added, followed by stirring for 10-60 min at 20-50° C. The activated charcoal was removed and the solution was finely filtered. The filtrate was aliquoted into 1-10 ml ampules and sterilized.

Example 27

Preparation method of lyophilized injection dosages with large volume is as follows.

| | |
|---|---|
| (−)-Huperzine A | 0.1% |
| Sodium chloride | 0.5% |
| Dilute hydrochloric acid | Suitable amount |

The rest is injectable grade water. (Each unit bottle contains 30-200 μg of (−)-huperzine A.)

A proper amount of injectable grade water was added into the above excipients. The pH was adjusted to 5-7 until complete dissolution. Water was added until it reached the mark and 0.1-0.5% of activated charcoal was added, followed by stirring for 10-60 min at 20-50° C. The activated charcoal was removed and the solution was finely filtered. The filtrate was aliquoted into 100-1000 ml injection containers and sterilized.

Example 28

1) Forming a salt between (±)-huperzine A and a chiral acid to give (−)-huperzine A-chiral acid salt; and 2) Basifying the (−)-huperzine A-chiral acid salt to give (−)-huperzine A.

The chiral acid in step 1) is D-dibenzoyl tartaric acid. The salt is formed by reaction of (±)-huperzine A with the chiral acid in a solvent, wherein the molar ratio of (±)-huperzine A/chiral acid is 1:0.5. The solvent is ethanol. The reaction conditions are as follows.

(±)-Huperzine A was suspended in a solvent with a ratio of 1:5. After the solution was homogeneously mixed by stirring, the chiral acid was added. After stirring for 0.5 h, the mixture was filtered and the solid was recrystallized. (−)-Huperzine A-chiral acid salt was obtained.

The solvent used for recrystallization was acetone.

The basifying method in step 2) is as follows.

The (−)-huperzine A-chiral acid salt was added into water at a ratio of 1:2. After the mixture was homogeneously mixed by stirring, a solution of 40% sodium hydroxide was used to adjust the pH value to 9.0-9.3. After crystals were precipitated, the suspension was filtered to give a solid. The solid was recrystallized from 95% ethanol and then dried to obtain (−)-huperzine A.

HPLC purity: 99.5% (310 nm), optical purity: 99.5%.

Example 29

1) Forming a salt between (±)-huperzine A and a chiral acid to give (−)-huperzine A-chiral acid salt; and 2) Basifying the (−)-huperzine A-chiral acid salt to give (−)-huperzine A.

The chiral acid in step 1) was tartaric acid. The salt was formed by reaction of (±)-huperzine A with the chiral acid in a solvent, wherein the molar ratio of (±)-huperzine A/chiral acid was 1:2. The solvent was acetic acid. The reaction conditions are as follows.

(±)-Huperzine A was suspended in a solvent at a ratio of 1:15. After the mixture was homogeneously mixed by stirring, the chiral acid was added. After stirring for 2 h, the resulting salt was filtered and recrystallized to give (−)-huperzine A-chiral acid salt.

The solvent used for recrystallization was ethanol.

The basifying method in step 2) is as follows.

The (−)-huperzine A-chiral acid salt was added into water at a ratio of 1:8. After the solution was homogeneously mixed by stirring, a solution of 40% sodium hydroxide was used to adjust the pH value to 9.0-9.3. After crystals were precipitated, the mixture was filtered to give a solid. The solid was recrystallized from 95% ethanol and then dried to obtain (−)-huperzine A. HPLC purity: 99.6% (310 nm), optical purity: 99.5%.

Example 30

1) Forming a salt between (±)-huperzine A and chiral acid to give (−)-huperzine A-chiral acid salt; and 2) Basifying the (−)-huperzine A-chiral acid salt to give (−)-huperzine A.

The chiral acid in step 1) was malic acid. The salt was formed by reaction of (±)-huperzine A with the chiral acid in a solvent, wherein the molar ratio of (±)-huperzine A/chiral acid was 1:1. The solvent was acetone. The reaction conditions are as follows.

(±)-Huperzine A was suspended in a solvent at a ratio of 1:10. After the solution was homogeneously mixed by stirring, the chiral acid was added. After stirring for 1 h, the resulting salt was filtered and recrystallized to get (−)-huperzine A-chiral acid salt.

The solvent used for recrystallization was ethyl acetate. The basifying method in step 2) is as follows.

The (−)-huperzine A-chiral acid salt was added into water at a ratio of 1:4. After the solution was homogeneously mixed by stirring, a solution of 40% sodium hydroxide was used to adjust the pH value to 9.0-10.0. After crystals were precipitated, the suspension was filtered to give a solid. The solid was recrystallized from 95% ethanol and dried to give (−)-huperzine A. HPLC purity: 99.5% (310 nm), optical purity: 99.5%.

Example 31

1) Forming a salt between (±)-huperzine A with a chiral acid to give (−)-huperzine A-chiral acid salt; and 2) Basifying the (−)-huperzine A-chiral acid salt to give (−)-huperzine A.

The chiral acid in step 1) was mandelic acid. The salt was obtained by reacting (±)-huperzine A with the chiral acid in a solvent, wherein the molar ratio of (±)-huperzine A/chiral acid was 1:0.8. The solvent was tetrahydrofuran.

The reaction conditions are as follows.

(±)-Huperzine A was suspended in a solvent with a ratio of 1:8. After the mixture was homogeneously mixed by stirring, the chiral acid was added. After stirring for 1.5 h, the solid was filtered and recrystallized to give (−)-huperzine A-chiral acid salt.

The solvent used for recrystallization was water. The basifying method in step 2) is as follows.

The (−)-huperzine A-chiral acid salt was added into water at a ratio of 1:6. After the mixture was homogeneously mixed by stirring, a solution of 40% sodium hydroxide was used to adjust the pH value to 9.0-9.3. After crystals were precipitated, the suspension was filtered to give a solid, which was recrystallized from 95% ethanol and then dried to obtain (−)-huperzine A. HPLC purity: 99.9% (310 nm), optical purity: 99.8%.

Example 32

1) Forming a salt between (±)-huperzine A with a chiral acid to give (−)-huperzine A-chiral acid salt; and 2) Basifying the (−)-huperzine A-chiral acid salt to give (−)-huperzine A.

The chiral acid in step 1) was camphor sulfonic acid. The salt was obtained by reacting (±)-huperzine A with the chiral acid in a solvent, wherein the molar ratio of (±)-huperzine A/chiral acid was 1:1.5. The solvent was acetone-water, wherein the acetone-water ratio was 1:1. The reaction conditions are as follows.

(±)-Huperzine A was suspended in a solvent with a ratio of 1:10. After the mixture was homogeneously mixed by stirring, the chiral acid was added. After stirring for 1 h, the resulting salt was filtered and recrystallized to give (−)-huperzine A-chiral acid salt.

The solvent used for recrystallization was selected from acetone, ethanol, ethyl acetate, water and a mixture thereof. The basifying method in step 2) is as follows.

The (−)-huperzine A-chiral acid salt was added into water at a ratio of 1:4. After the mixture was homogeneously mixed by stirring, a solution of 40% sodium hydroxide was used to adjust the pH value to 9.0-9.3. After crystals were precipitated, the suspension was filtered to give a solid, which was recrystallized from 95% ethanol and then dried to obtain (−)-huperzine A. HPLC purity: 99.5% (310 nm), optical purity: 99.5%.

Example 33

1) Forming a salt between (±)-huperzine A with a chiral acid to give (−)-huperzine A-chiral acid salt; and 2) Basifying the (−)-huperzine A-chiral acid salt to give (−)-huperzine A.

The chiral acid in step 1) was camphor sulfonic acid. The salt was obtained by reacting (±)-huperzine A with the chiral acid in a solvent, wherein the molar ratio of (±)-huperzine A/chiral acid was 1:1.5. The solvent was acetone-water, wherein the acetone-water ratio was 5:1. The reaction conditions are as follows.

(±)-Huperzine A was suspended in a solvent at a ratio of 1:10. After the mixture was homogeneously mixed by stirring, the chiral acid was added. After stirring for 1 h, the resulting salt was filtered and recrystallized to give (−)-huperzine A-chiral acid salt.

The solvent used for recrystallization was selected from acetone, ethanol, ethyl acetate, water and a mixture thereof. The basifying method in step 2) is as follows.

The (−)-huperzine A-chiral acid salt was added into water at a ratio of 1:4. After the mixture was homogeneously mixed by stirring, a solution of 40% sodium hydroxide was used to adjust the pH value to 9.0-9.3. After crystals were precipitated, the suspension was filtered to give a solid, which was recrystallized from 95% ethanol and then dried to obtain (−)-huperzine A. HPLC purity: 99.5% (310 nm), optical purity: 99.5%.

Example 34

1) Forming a salt between (±)-huperzine A with chiral acid to give (−)-huperzine A-chiral acid salt; and 2) Basifying the (−)-huperzine A-chiral acid salt to give (−)-huperzine A.

The chiral acid in step 1) was camphor sulfonic acid. The salt was obtained by reacting (±)-huperzine A with the chiral acid in a solvent, wherein the molar ratio of (±)-huperzine A/chiral acid was 1:1.5. The solvent was mixed ethanol-water, wherein the ethanol-water ratio was 1:1. The reaction conditions are as follows.

(±)-Huperzine A was suspended in the solvent at a ratio of 1:10. After the solution was homogeneously mixed by stirring, the chiral acid was added. After stirring for 1 h, the solid was filtered and recrystallized to give (−)-huperzine A-chiral acid salt.

The solvent used for recrystallization was selected from acetone, ethanol, ethyl acetate, water and a mixture thereof. The basifying method in step 2) is as follows.

The (−)-huperzine A-chiral acid salt was added into water at a ratio of 1:4. After the solution was homogeneously mixed by stirring, a solution of 40% sodium hydroxide was used to adjust the pH value to 9.0-9.3. After crystals were precipitated, the suspension was filtered to give a solid, which was recrystallized from 95% ethanol and then dried to give (−)-huperzine A. HPLC purity: 99.5% (310 nm), optical purity: 99.5%.

Example 35

1) Forming a salt between (±)-huperzine A with a chiral acid to give (−)-huperzine A-chiral acid salt; and 2) Basifying the (−)-huperzine A-chiral acid salt to give (−)-huperzine A.

The chiral acid in step 1) was camphor sulfonic acid. The salt was obtained by reacting (±)-huperzine A with the chiral acid in a solvent, wherein the molar ratio of (±)-huperzine A/chiral acid was 1:1.5. The solvent was mixed ethanol-water, wherein the ethanol-water ratio was 5:1. The reaction conditions are as follows.

(±)-Huperzine A was suspended in the solvent at a ratio of 1:10. After the solution was homogeneously mixed by stirring, the chiral acid was added. After stirring for 1 h, the solid was filtered and recrystallized to give (−)-huperzine A-chiral acid salt.

The solvent used for recrystallization was selected from acetone, ethanol, ethyl acetate, water and a mixture thereof.

The basifying method in step 2) is as follows.

The (−)-huperzine A-chiral acid salt was added into water at a ratio of 1:4. After the solution was homogeneously mixed by stirring, a solution of 40% sodium hydroxide was used to adjust the pH value to 9.0-9.3. After crystals were precipitated, the suspension was filtered to give a solid, which was recrystallized from 95% ethanol and then dried to give (−)-huperzine A.

HPLC purity: 99.5% (310 nm), optical purity: 99.5%.

Example 36

(±)-Huperzine A was suspended in the mixed solvent of acetone-water, wherein the acetone-water ratio was 1:1 (v:v). The weight ratio of (±)-huperzine A/solvent was 1:5. D-(−)-dibenzoyl tartaric acid was then added to form a salt, wherein the molar ratio of (±)-huperzine A/chiral acid was 1:0.5. After formation of salt, the solid was filtered, washed and dried to obtain (±)-huperzine A-chiral acid salt. The salt was added into water at a weight ratio of 1:2. After the solution was homogeneously mixed by stirring, the pH value of the solution was adjusted to 9.0-10.0 by using a sodium hydroxide solution. After crystals were precipitated, the mixture was filtered to give a solid, which was then dried to give (−)-huperzine A. The yield was higher than 70%, the optical purity was higher than 99.5% and the chemical purity was higher than 99.5%.

Example 37

(±)-Huperzine A was suspended in the mixed solvent of acetone-water, wherein the acetone-water ratio was 5:1 (v:v). The weight ratio of (±)-huperzine A/solvent was 1:15. D-(−)-dibenzoyl tartaric acid was then added to form a salt, wherein the molar ratio of (±)-huperzine A/chiral acid is 1:2. After formation of salt, the solid was filtered, washed and dried to give (±)-huperzine A-chiral acid salt. The salt was added into water at a weight ratio of 1:8. After the solution was homogeneously mixed by stirring, the pH value of the solution was adjusted to 9.0-10.0 by using a sodium hydroxide solution. After crystals were precipitated, the mixture was filtered to give a solid, which was then dried to give (−)-huperzine A. The yield was higher than 70%, the optical purity was higher than 99.5% and the chemical purity was higher than 99.5%.

Example 38

(±)-Huperzine A was suspended in the mixed solvent of ethanol-water, wherein the ethanol-water ratio was 1:1 (v:v). The weight ratio of (±)-huperzine A/solvent was 1:5. D-(−)-dibenzoyl tartaric acid was then added to form a salt, wherein the molar ratio of (±)-huperzine A/chiral acid was 1:0.5. After formation of salt, the solid was filtered, washed and dried to give (±)-huperzine A-chiral acid salt. The salt was added into water at a weight ratio of 1:2. After the solution was homogeneously mixed by stirring, the pH value of the solution was adjusted to 9.0-10.0 by using a sodium hydroxide solution. After crystals were precipitated, the mixture was filtered to give a solid, which was then dried to give (−)-huperzine A. The yield was higher than 70%, the optical purity was higher than 99.5% and the chemical purity was higher than 99.5%.

Example 39

(±)-Huperzine A was suspended in the mixed solvent of ethanol-water, wherein the ethanol-water ratio was 5:1 (v:v). The weight ratio of (±)-huperzine A/solvent was 1:15. D-(−)-dibenzoyl tartaric acid was then added to form a salt, wherein the molar ratio of (±)-huperzine A/chiral acid was 1:2. After formation of salt, the solid was filtered, washed and dried to give (±)-huperzine A-chiral acid salt. The salt was added into water at a weight ratio of 1:8. After the solution was homogeneously mixed by stirring, the pH value of the solution was adjusted to 9.0-10.0 by using a sodium hydroxide solution. After crystals were precipitated, the resulting salt was filtered to give a solid, which was then dried to give (−)-huperzine A. The yield was higher than 70%, the optical purity was higher than 99.5% and the chemical purity was higher than 99.5%.

Example 40

(±)-Huperzine A was suspended in the mixed solvent of ethanol-water, wherein the ethanol-water ratio was 2.5:1 (v:v). The weight ratio of (±)-huperzine A/solvent was 1:10. D-(−)-dibenzoyl tartaric acid was then added to form a salt, wherein the molar ratio of (±)-huperzine A/chiral acid was 1:1. After stirring for 1 h, the mixture was filtered. The solid was recrystallized from anhydrous ethanol to give (−)-huperzine A dibenzoyltartaric acid salt. (−)-Huperzine A dibenzoyltartaric acid salt was added into water at a weight ratio of 1:4. A solution of 40% sodium hydroxide was used to adjust the pH value to 9.0-9.3. The resulting salt was filtered and then dried under vacuum to give (−)-Huperzine A.

The recovery yield of the product was higher than 90%, the optical purity was higher than 99.8% and the chemical purity was higher than 99.8%.

What is claimed is:

1. A method of synthesizing (−)-huperzine A, said method comprising the following steps:
   (a) Forming a salt between (±)-huperzine A and a chiral acid to give (−)-huperzine A-chiral acid salt; and
   (b) Basifydng the (−)-huperzjne A-chiral acid salt to give (−)-huperzine A;
   wherein said chiral acid in step (a) is selected from D-dibenzoyl tartaric acid and D-tartaric acid; wherein step (a) is performed in a solvent selected from acetone-water and ethanol-water; and wherein the ratio of ethanol-water ranges from 1:1 to 5:1.

2. The method of claim 1, wherein said chiral acid in step (a) is D-dibenzoyl tartaric acid; wherein the ratio of acetone-water is 1:1 to 5:1; wherein the ratio of ethanol-water is 1:1 to 5:1; and wherein the molar ratio of (±)-huperzine A to chiral acid ranges from 1:0.5 to 1:2.

3. The method of claim 1, wherein the ratio of acetone-water is 1:1 to 3:1; wherein the ratio of ethanol-water is 1:1 to 3:1; and wherein the molar ratio of (±)-huperzine A to chiral acid ranges from 1:0.75 to 1:1.5.

4. The method of claim 1, wherein the ratio of acetone-water is 1:1; wherein the ratio of ethanol-water is 1:1; and wherein the molar ratio of (±)-huperzine A to chiral acid ranges from 1:0.8 to 1:0.9.

5. The method of claim 1, wherein:
(±)-huperzlne A is suspended in acetone-water or ethanol-water, wherein the ratio of acetone-water is 1:1 to 5:1, the ratio of ethanol-water is 1:1 to 5:1, and the weight ratio of (±)-huperzine A-solvent is 1:5 to 1:15;
D-dibenzoyl tartaric acid is then added for salt formation, wherein the molar ratio of (±)-huperzine A to chiral acid ranges from 1:0.5 to 1:2;
the resulting salt is filtered, washed and then dried to give (−)-huperzine A chiral acid salt;
the salt is added to water and thoroughly mixed, wherein the weight ratio of the salt to water ranges from 1:2 to 1:8;
aqueous sodium hydroxide is used to adjust the pH value to a range of 9.0 to 9.3;
and the precipitated crystal is filtered to give a solid, which is then dried to give (−)-huperzine A.

6. The method of claim 1, wherein:
(±)-huperzine A is suspended in ethanol-water, wherein the ratio of ethanol-water is 2.5:1; wherein the weight ratio of (±)-huperzine A to solvent is 1:10;
D-dibenzoyl tartaric acid is then added for salt formation, wherein the molar ratio of (±)-huperzine A to chiral acid is 1:1;
the mixture is stirred for one hour and then filtered, and the fltered solid is recrystallized from anhydrous ethanol to give (−)-huperzine A-D-dibenzoyl tartaric acid salt;
the (−)-huperzine A-D-dibenzoyl tartaric acid salt is added to water and thoroughly mixed, wherein the weight ratio of the salt to water is 1:4;
aqueous sodium hydroxide is used to adjust the pH value to a range of 9.0 to 9.3; and
the resulting solid is filtered and vacuum dried to give (−)-huperzine A.

7. The method of claim 1, wherein said (−)-huperzine A obtained after step (b) has a purity higher than 99.5%.

8. The method of claim 1, wherein said (−)-huperzine A obtained after step (b) comprises 0.01% to 0.03% of impurity (I):

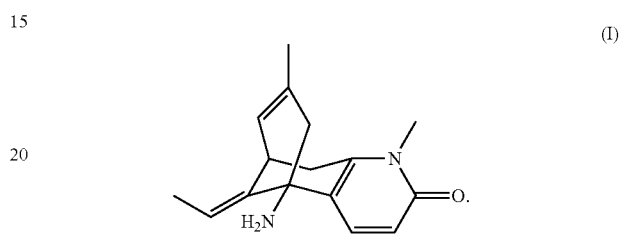

9. The method of claim 1, wherein said (−)-huperzine A obtained after step (b) is formulated in the form of a tablet, capsule, granule, pill, oral liquid or injection.

10. The method of claim 1, wherein said (−)-huperzine A is useful for improving learning and memory efficiency, restoring the functions of damaged neurons, treating myasthenia gravis, schizophrenia, dementia, benign memory impairment, amnesia and senile dementia, and improving children's memories.

* * * * *